(12) United States Patent
Cupp et al.

(10) Patent No.: US 6,927,279 B2
(45) Date of Patent: Aug. 9, 2005

(54) ANTITHROMBIN NUCLEOTIDES AND PROTEINS FROM HORN FLY

(75) Inventors: Eddie Wayne Cupp, Auburn, AL (US); Mary Smith Cupp, Auburn, AL (US)

(73) Assignee: Auburn University, Auburn, AL (US)

( * ) Notice: Subject to any disclaimer, the term of this patent is extended or adjusted under 35 U.S.C. 154(b) by 296 days.

(21) Appl. No.: 10/200,659

(22) Filed: Jul. 22, 2002

(65) Prior Publication Data

US 2003/0114654 A1 Jun. 19, 2003

Related U.S. Application Data

(62) Division of application No. 09/376,113, filed on Aug. 17, 1999, now Pat. No. 6,451,992.
(60) Provisional application No. 60/097,227, filed on Aug. 20, 1998.

(51) Int. Cl.[7] .................................................. C07K 1/00
(52) U.S. Cl. ..................... 530/350; 530/300; 530/412; 435/7.1; 435/7.2; 435/70.1; 435/70.4; 435/69.1; 424/178.1; 514/2; 514/12; 514/21
(58) Field of Search .................................. 530/350, 300, 530/412, 387.1, 806; 435/7.1, 7.2, 70.1, 70.4, 69.1; 424/178.1; 514/2, 12, 21

(56) References Cited

FOREIGN PATENT DOCUMENTS

WO    WO 98/21324    5/1998

OTHER PUBLICATIONS

Cupp et al., Journal of Medical Entomology, vol. 34, No. 2, pp. 87–94, 1997.*
Byford et al., "A Review of Ectoparasites and Their Effect on Cattle Production,"0 *J. Anim. Sci*, 1992, 70:597–602.
Cappello et al., "Isolation and Characterization of the Tsetse Thrombin Inhibitor: A Potent Antithrombotic Peptide from the Saliva of Glossina Morsitans," *Am. J. Trop. Med. Hyg.*, 1996, 54(5):475–80.
Cappello et al., ERRATUM, *Am. J. Trop. Med. Hyg.*, 1996, 55(1) 118.
Cupp et al., "Blood–Feeding Strategy of Haematobia Irritans (Diptera: Muscidae)," *Journal of Medical Entomology*, 1998, 35(4) 591–5.
Harris et al., "Horn Flies and Stable Flies: Feeding Activity," *Annals of the Entomological Society of America*, 1974, 67(6):891–894.
Kerlin et al., (1992), "Acquired Immune Response of Cattle Exposed to Buffalo Fly (*Haematobia Irritans Exigua*)," *Veterinary Parasitology*, 1992, 43:115–129.
Lewis et al., "Polynucleotide Vaccines In Animals: Enhancing and Modulating Responses," *Vaccine*, 1997, 15(8):861–864.
Schwinghammer et al., "Psyciological and Nutritional Response of Beef Steers to Infestations of the Hom Fly (Diptera: Muscidae)," *Journal of Economic* Entomology, 1986, 79(4):1010–1014.
Tighe et al., (1998), "Gene Vaccination: Plasmid DNA Is More Than Just A Blueprint," *Immunology Today*, 1998, 19(2):89–97.

* cited by examiner

*Primary Examiner*—Jon Weber
*Assistant Examiner*—Hope A. Robinson
(74) *Attorney, Agent, or Firm*—Alston & Bird LLP

(57) ABSTRACT

Compositions and methods for preventing hematophagous infestation of cattle are provided, directed at isolated proteins with antithrombin activity and nucleotide sequences encoding the proteins. The protein named thrombostasin is isolated from the salivary glands of *Haematobia irritans*. The compositions are useful as veterinary vaccines in prevention of blood-feeding in cattle by the infesting horn fly. The proteins of the invention are also useful in treatment of thrombosis.

13 Claims, 5 Drawing Sheets

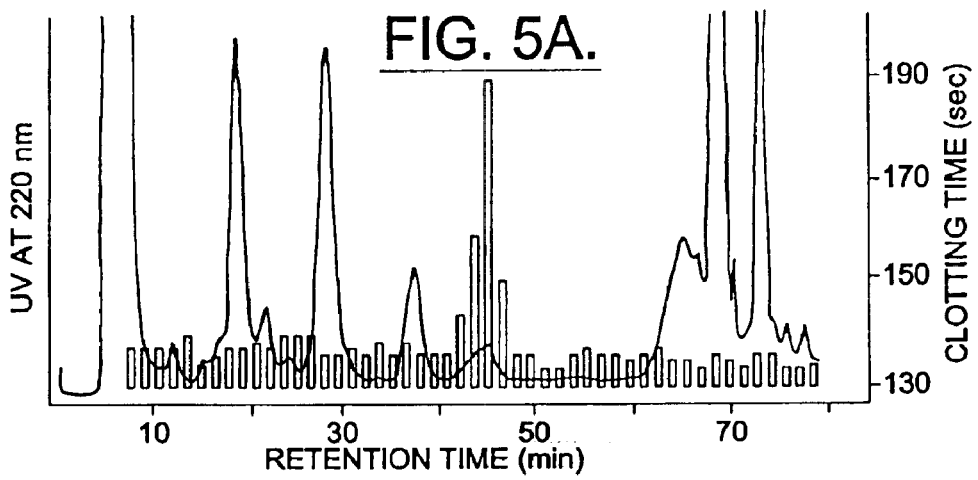
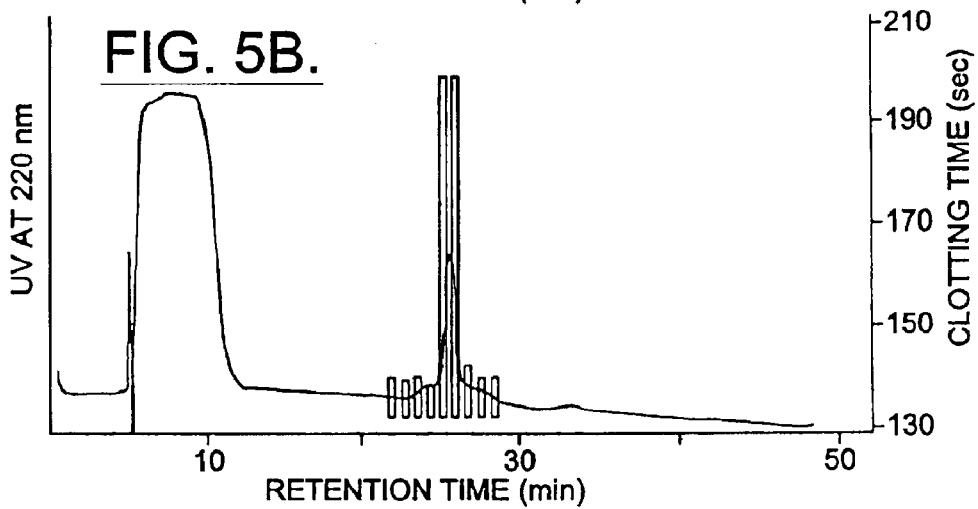
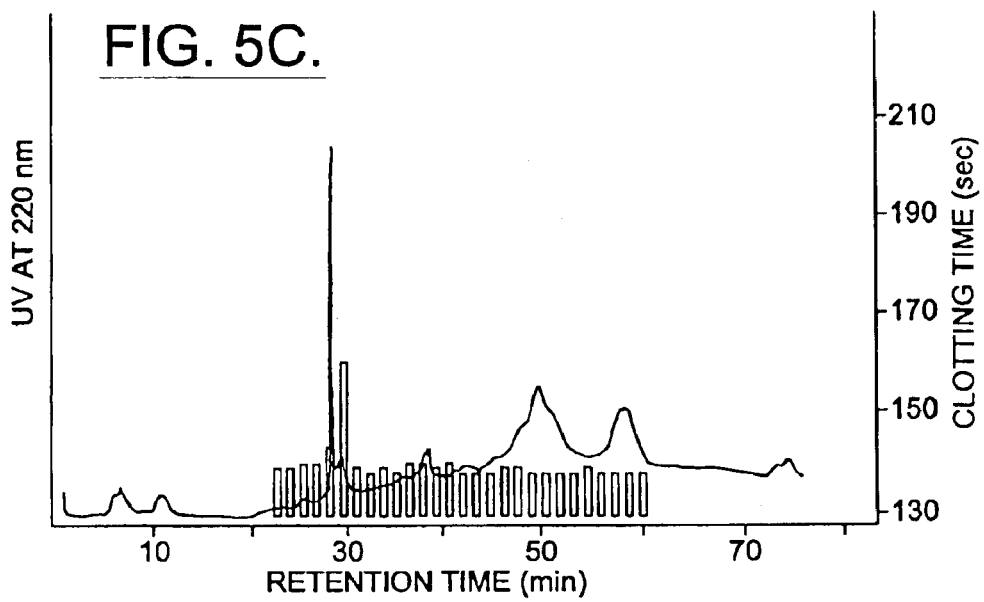

SEQUENCE LISTING

```
<160> NUMBER OF SEQ ID NOS: 7

<210> SEQ ID NO 1
<211> LENGTH: 370
<212> TYPE: DNA
<213> ORGANISM: Haematobia irritans
<220> FEATURE:
<221> NAME/KEY: CDS
<222> LOCATION: (1)...(243)

<400> SEQUENCE: 1
```

```
agt gcg ggt ccc atc aca ctg caa tta gat gat gat gat gat gac gac      48
Ser Ala Gly Pro Ile Thr Leu Gln Leu Asp Asp Asp Asp Asp Asp Asp
 1               5                  10                  15 tct ggt atc ccc ata ttt gaa atg gat gat gaa gat gaa gac tct aat      96
Ser Gly Ile Pro Ile Phe Glu Met Asp Asp Glu Asp Glu Asp Ser Asn
                20                  25                  30 gac aat caa aaa ttt cct tta agt ttt gaa cgg ttt cca gaa aat gaa     144
Asp Asn Gln Lys Phe Pro Leu Ser Phe Glu Arg Phe Pro Glu Asn Glu
            35                  40                  45 aaa aat caa gta ggc ttg aga gct aga ttt aac aaa ttc atg gca aaa     192
Lys Asn Gln Val Gly Leu Arg Ala Arg Phe Asn Lys Phe Met Ala Lys
 50                  55                  60 ttt act tcg ctg ttt ggc cgt cgt cgt ggc gta aat gtt ccc aat gct     240
Phe Thr Ser Leu Phe Gly Arg Arg Arg Gly Val Asn Val Pro Asn Ala
 65                  70                  75                  80 gca taagcaaact aatattatat attaattact tcatttatgt gttctacact          293
Ala atataacaaa taaaggatt attaattaat tcataaaaaa aaaaaaaaaa aaaaaaaaa     353 aaaaaaaaaa aaaaaaa                                                  370

<210> SEQ ID NO 2
<211> LENGTH: 81
<212> TYPE: PRT
<213> ORGANISM: Haematobia irritans

<400> SEQUENCE: 2

Ser Ala Gly Pro Ile Thr Leu Gln Leu Asp Asp Asp Asp Asp Asp Asp
 1               5                  10                  15

Ser Gly Ile Pro Ile Phe Glu Met Asp Asp Glu Asp Glu Asp Ser Asn
                20                  25                  30

Asp Asn Gln Lys Phe Pro Leu Ser Phe Glu Arg Phe Pro Glu Asn Glu
            35                  40                  45

Lys Asn Gln Val Gly Leu Arg Ala Arg Phe Asn Lys Phe Met Ala Lys
 50                  55                  60

Phe Thr Ser Leu Phe Gly Arg Arg Arg Gly Val Asn Val Pro Asn Ala
 65                  70                  75                  80

Ala

<210> SEQ ID NO 3
<211> LENGTH: 30
<212> TYPE: PRT
<213> ORGANISM: Haematobia irritans

<400> SEQUENCE: 3

Ser Ala Gly Pro Ile Thr Leu Gln Leu Asp Asp Asp Asp Asp Asp Asp
 1               5                  10                  15

Ser Gly Ile Pro Ile Phe Glu Met Asp Asp Glu Asp Glu Glu
                20                  25                  30

<210> SEQ ID NO 4
<211> LENGTH: 611
<212> TYPE: DNA
<213> ORGANISM: Haematobia Irritans
<220> FEATURE:
<221> NAME/KEY: CDS
<222> LOCATION: (2)...(505)

<400> SEQUENCE: 4 t gga atc tta gct ctt tca gct gtc tgc cag gcc caa aat gtc tta tca   49
```

```
      Gly Ile Leu Ala Leu Ser Ala Val Cys Gln Ala Gln Asn Val Leu Ser
       1               5                  10                  15 gga cgc cgc caa cat ggt gcc caa gga ctt tct gga tat tct ggt gat             97
Gly Arg Arg Gln His Gly Ala Gln Gly Leu Ser Gly Tyr Ser Gly Asp
             20                  25                  30 aat gac tgg gga tat tac ggt gaa gcc gga gct cca gga tcg gac tac            145
Asn Asp Trp Gly Tyr Tyr Gly Glu Ala Gly Ala Pro Gly Ser Asp Tyr
         35                  40                  45 tct ggt tct tca ggt caa tgg gca ccc tta gat ttt gat tat aac agt            193
Ser Gly Ser Ser Gly Gln Trp Ala Pro Leu Asp Phe Asp Tyr Asn Ser
     50                  55                  60 cta cct gga tta tcg gga tat aac cat gaa caa caa gat tac gaa gaa            241
Leu Pro Gly Leu Ser Gly Tyr Asn His Glu Gln Gln Asp Tyr Glu Glu
 65                  70                  75                  80 gat agt tat cgc cat gta cgc agt gcg ggt ccc atc aca ctg caa tta            289
Asp Ser Tyr Arg His Val Arg Ser Ala Gly Pro Ile Thr Leu Gln Leu
                 85                  90                  95 gat gat gat gat gat gac gac tct ggt atc ccc ata ttt gaa atg gat            337
Asp Asp Asp Asp Asp Asp Asp Ser Gly Ile Pro Ile Phe Glu Met Asp
             100                 105                 110 gat gaa gat gta gac tct aat gac aat caa aaa ttt cct tta agt ttt            385
Asp Glu Asp Val Asp Ser Asn Asp Asn Gln Lys Phe Pro Leu Ser Phe
         115                 120                 125 gaa cgg ttt cca gaa aat gaa aaa aat caa gta ggc ttg aga gct aga            433
Glu Arg Phe Pro Glu Asn Glu Lys Asn Gln Val Gly Leu Arg Ala Arg
     130                 135                 140 ttt aac aaa ttc atg gca aaa ttt act tcg ctg ttt ggc cgt cgt cgt            481
Phe Asn Lys Phe Met Ala Lys Phe Thr Ser Leu Phe Gly Arg Arg Arg
145                 150                 155                 160 ggc gta aat gtt ccc aat gct gca taagcaaact aatattatat attaattact           535
Gly Val Asn Val Pro Asn Ala Ala
                 165 tcatttatgt gttctacact atataacaaa taaaaggatt attaattaat tcataaaaaa          595 aaaaaaaaaa aaaaaa                                                          611

<210> SEQ ID NO 5
<211> LENGTH: 168
<212> TYPE: PRT
<213> ORGANISM: Haematobia Irritans

<400> SEQUENCE: 5

Gly Ile Leu Ala Leu Ser Ala Val Cys Gln Ala Gln Asn Val Leu Ser
 1               5                  10                  15

Gly Arg Arg Gln His Gly Ala Gln Gly Leu Ser Gly Tyr Ser Gly Asp
             20                  25                  30

Asn Asp Trp Gly Tyr Tyr Gly Glu Ala Gly Ala Pro Gly Ser Asp Tyr
         35                  40                  45

Ser Gly Ser Ser Gly Gln Trp Ala Pro Leu Asp Phe Asp Tyr Asn Ser
     50                  55                  60

Leu Pro Gly Leu Ser Gly Tyr Asn His Glu Gln Gln Asp Tyr Glu Glu
 65                  70                  75                  80

Asp Ser Tyr Arg His Val Arg Ser Ala Gly Pro Ile Thr Leu Gln Leu
                 85                  90                  95

Asp Asp Asp Asp Asp Asp Asp Ser Gly Ile Pro Ile Phe Glu Met Asp
             100                 105                 110

Asp Glu Asp Val Asp Ser Asn Asp Asn Gln Lys Phe Pro Leu Ser Phe
         115                 120                 125
```

-continued

```
Glu Arg Phe Pro Glu Asn Glu Lys Asn Gln Val Gly Leu Arg Ala Arg
    130                 135                 140
Phe Asn Lys Phe Met Ala Lys Phe Thr Ser Leu Phe Gly Arg Arg Arg
145                 150                 155                 160
Gly Val Asn Val Pro Asn Ala Ala
                165
```

<210> SEQ ID NO 6
<211> LENGTH: 631
<212> TYPE: DNA
<213> ORGANISM: Haematobia Irritans
<220> FEATURE:
<221> NAME/KEY: CDS
<222> LOCATION: (1)...(525)

<400> SEQUENCE: 6

| | | |
|---|---|---|
| atg aag cat ttc gta gtt att gga atc tta gct ctt tca gct gtc tgc<br>Met Lys His Phe Val Val Ile Gly Ile Leu Ala Leu Ser Ala Val Cys<br>1               5                  10                  15 | 48 |
| cag gcc caa aat gtc tta tca gga cgc cgc caa cat ggt gcc caa gga<br>Gln Ala Gln Asn Val Leu Ser Gly Arg Arg Gln His Gly Ala Gln Gly<br>            20                  25                  30 | 96 |
| ctt tct gga tat tct ggt gat aat gac tgg gga tat tac ggt gaa gcc<br>Leu Ser Gly Tyr Ser Gly Asp Asn Asp Trp Gly Tyr Tyr Gly Glu Ala<br>        35                  40                  45 | 144 |
| gga gct cca gga tcg gac tac tct ggt tct tca ggt caa tgg gca ccc<br>Gly Ala Pro Gly Ser Asp Tyr Ser Gly Ser Ser Gly Gln Trp Ala Pro<br>    50                  55                  60 | 192 |
| tta gat ttt gat tat aac agt cta cct gga tta tcg gga tat aac cat<br>Leu Asp Phe Asp Tyr Asn Ser Leu Pro Gly Leu Ser Gly Tyr Asn His<br>65                  70                  75                  80 | 240 |
| gaa caa caa gat tac gaa gaa gat agt tat cgc cat gta cgc agt gcg<br>Glu Gln Gln Asp Tyr Glu Glu Asp Ser Tyr Arg His Val Arg Ser Ala<br>                85                  90                  95 | 288 |
| ggt ccc atc aca ctg caa tta gat gat gat gat gat gac gac tct ggt<br>Gly Pro Ile Thr Leu Gln Leu Asp Asp Asp Asp Asp Asp Asp Ser Gly<br>            100                 105                 110 | 336 |
| atc ccc ata ttt gaa atg gat gat gaa gat gta gac tct aat gac aat<br>Ile Pro Ile Phe Glu Met Asp Asp Glu Asp Val Asp Ser Asn Asp Asn<br>        115                 120                 125 | 384 |
| caa aaa ttt cct tta agt ttt gaa cgg ttt cca gaa aat gaa aaa aat<br>Gln Lys Phe Pro Leu Ser Phe Glu Arg Phe Pro Glu Asn Glu Lys Asn<br>    130                 135                 140 | 432 |
| caa gta ggc ttg aga gct aga ttt aac aaa ttc atg gca aaa ttt act<br>Gln Val Gly Leu Arg Ala Arg Phe Asn Lys Phe Met Ala Lys Phe Thr<br>145                 150                 155                 160 | 480 |
| tcg ctg ttt ggc cgt cgt cgt ggc gta aat gtt ccc aat gct gca<br>Ser Leu Phe Gly Arg Arg Arg Gly Val Asn Val Pro Asn Ala Ala<br>                165                 170                 175 | 525 |
| taagcaaact aatattatat attaattact tcatttatgt gttctacact atataacaaa | 585 |
| taaaaggatt attaattaat tcataaaaaa aaaaaaaaaa aaaaaa | 631 |

<210> SEQ ID NO 7
<211> LENGTH: 175
<212> TYPE: PRT
<213> ORGANISM: Haematobia Irritans

<400> SEQUENCE: 7

```
Met Lys His Phe Val Val Ile Gly Ile Leu Ala Leu Ser Ala Val Cys
1               5                  10                  15
```

-continued

```
Gln Ala Gln Asn Val Leu Ser Gly Arg Arg Gln His Gly Ala Gln Gly
            20                  25              30

Leu Ser Gly Tyr Ser Gly Asp Asn Asp Trp Gly Tyr Tyr Gly Glu Ala
        35              40              45

Gly Ala Pro Gly Ser Asp Tyr Ser Gly Ser Ser Gly Gln Trp Ala Pro
    50              55              60

Leu Asp Phe Asp Tyr Asn Ser Leu Pro Gly Leu Ser Gly Tyr Asn His
65              70              75              80

Glu Gln Gln Asp Tyr Glu Glu Asp Ser Tyr Arg His Val Arg Ser Ala
            85              90              95

Gly Pro Ile Thr Leu Gln Leu Asp Asp Asp Asp Asp Asp Ser Gly
            100             105             110

Ile Pro Ile Phe Glu Met Asp Asp Glu Asp Val Asp Ser Asn Asp Asn
        115             120             125

Gln Lys Phe Pro Leu Ser Phe Glu Arg Phe Pro Glu Asn Glu Lys Asn
    130             135             140

Gln Val Gly Leu Arg Ala Arg Phe Asn Lys Phe Met Ala Lys Phe Thr
145             150             155             160

Ser Leu Phe Gly Arg Arg Arg Gly Val Asn Val Pro Asn Ala Ala
                165             170             175
```

ANTITHROMBIN NUCLEOTIDES AND PROTEINS FROM HORN FLY

CROSS-REFERENCE TO RELATED APPLICATION

This application is a divisional of U.S. application Ser. No. 09/376,113 filed Aug. 17, 1999, now issued as U.S. Pat. No. 6,451,992, which claims the benefit of U.S. Provisional Application No. 60/097,227, filed Aug. 20, 1998, which is hereby incorporated herein in its entire by reference.

FIELD OF THE INVENTION

The invention relates to veterinary vaccines for prevention of hematophagous infestation of cattle and medical treatment of thrombosis.

BACKGROUND OF THE INVENTION

Losses in livestock production in the United States due to ectoparasite infestations have been estimated to exceed $2.26 billion annually (Byford et al. (1992) *J. Anim. Sci.* 70:597–602). Of the five to six major arthropod pest species involved, the horn fly *Haematobia irritans linnaeus* is the most significant and widespread. Its annual economic impact on cattle production in the U.S.A. has been estimated at $730.3 million. In Canada, control of this ectoparasite in cattle production has been estimated to reduce losses by $71–107 million per year using 1977 dollar values (Haufe and Weintraub (1985) *Can. Entomol.* 117:901–907). Thus in North America, the annual economic impact on cattle production by this blood-sucking fly approaches $1 billion.

Physiological manifestations of hornfly infestation include an increase in heart rates, respiration rates, and rectal temperatures. Additionally, water consumption and urine production are significantly increased as well as urinary nitrogen secretion. Blood cortisol concentrations are also significantly increased. Decreased weight gain, increased activity, and decreased grazing have also been reported. (Schwinghammer et al. (1986) *J. Econ. Entomol.* 79:1010–1014).

The adult stage of both sexes of *H. irritans* are obligate ectoparasites that blood-feed intermittently during the 24 hours of the day. Unlike other dipterous pests that are transient blood-feeders, (black flies, mosquitoes, horse flies, stable flies), the winged adults of *H. irritans* remain on the bovine host and, when needing nourishment, recurrently insert their mouthparts into the skin to feed. Harris et al. (1974) *Ann. Entomol. Soc. Am.* 67:891–894, noted that under experimental conditions, female horn flies spent an average of 163 minutes/day feeding; males averaged 96 minutes per day. Each female ingested an average of 17.1 mg of blood per day while males imbibed 12.1 mg/individual due to the difference in feeding times (Harris and Frazer (1970) *Ann. Entomol. Soc. Am.* 63:1475–1476).

The scientific literature describing the salivary gland physiology of *H. irritans*, particularly with reference to blood-feeding, is sparse. Hori et al. (1981) *Appl. Ent. Zool,* 16:16–23, has compared several categories of digestive enzymes in the gut and salivary glands of *H. irritans* with *Stomoxys calcitrans* (*Linnaeus*), the stable fly. Weak aminopeptidase activity was detected in *H. irritans* saliva, suggesting that proteases and glycosidases in the gut are exclusively responsible for digestion of blood.

The horn fly *Haematobia irritans linnaeus* is a subspecies with *H. i. exigua de Meijere*, the buffalo fly that occurs in Australia and elsewhere in the southern hemisphere. Kerlin and Hughes (1992) *Med. Vet. Entomol.* 6:121–126, have compared enzymes in the saliva of four parasitic arthropods—*H. irritans exigua*, *Boophilus microplus* (Canestrini), *Aedes aegypti* (Linnaeus), and *Lucilia cuprina* (Wiedemann) and noted differences in enzyme profiles of saliva between the four species that apparently reflect their dissimilar feeding strategies. These differences were mainly in the type and levels of glycosidase and protease activities. *H. irritans* exigua saliva, collected by serotonin stimulation and then evaluated by SDS polyacrylamide gel electrophoresis, produced 7–8 bands by silver staining. Apyrase activity in saliva and salivary gland extracts (SGEs) of this species was marginally detectable, suggesting that this subspecies does not prevent bovine platelet aggregation in the same way as many other blood-feeding arthropods (Ribeiro (1987) *Ann. Rev. Entomol.* 32:463–478).

Furthermore, investigation of immune response of cattle exposed to *H. irritans* exigua showed production of high levels of circulating antibodies to some but not all of the buffalo fly antigens; nevertheless, flies feeding on previously exposed cattle did not exhibit higher mortality than those fed on unexposed cattle. (Kerlin and Allingham (1992) *Vet. Parasitol.* 43:115–129).

Elucidation of biochemical strategies adopted by blood-feeding arthropods has advanced in the past decade. Although the presence of anticoagulants in saliva of hematophagous arthropods has been known for at least eight decades, only recently have some of the active components been purified and their molecular structures defined. It has become apparent that coagulation factors such as factors Xa and thrombin (factor II), which occur at a nexus in the coagulation cascade, are frequently targeted.

Studies of saliva from several species of black flies have suggested that specific enzyme targets may be associated with host selection (Abebe et al. (1994)). For example, data for zoophagic species that prefer cattle indicate that thrombin is an important target molecule whose inactivation may also prevent irreversible platelet aggregation in addition to impeding the coagulation cascade. See Hudson (1964) *Can. J. Zool.* 42:113–120, for *Stomoxys calcitrans*; and Parker and Mant (1979) *Thrombos. Haemostas* (Stuttg.) 42:743–751, on *G. morsitans* (Westwood) saliva.

Because of the adverse impact of the above-described ectoparasitic infestation in cattle, there is a therapeutic and economic need for preventing such infestation.

There is also need for treatment of thromboembolic diseases. Thromboembolic diseases are among the most important circulatory diseases. A thrombus is a blood clot that partially or completely blocks blood flow through a blood vessel. An embolus is a thrombus that has formed elsewhere in the body, broken free, and traveled to the site where blockage occurs. Blockage in the brain results in a stroke, i.e., a cerebral infarction, a localized area of dead cells. An embolus in a lung can produce pulmonary embolism, one of the principal lung diseases in bed-ridden patients. Bed ridden and elderly persons are also particularly prone to thrombophlebitis, which is a blockage of circulation in a leg caused by an embolus. An embolus or thrombus lodging in one of the blood vessels serving the heart causes necrosis of part of the heart tissue, a myocardial infarction, commonly called a heart attack.

The initiating event of many myocardial infarctions is the hemorrhage into atherosclerotic plaques. Such hemorrhage often results in the formation of a thrombus (or blood clot) in the coronary artery which supplies the infarct zone. This thrombus is composed of a combination of fibrin and blood platelets. The formation of a fibrin-platelet clot has serious clinical ramifications. The degree and duration of the occlusion caused by the fibrin-platelet clot determines the mass of the infarct zone and the extent of damage.

The formation of fibrin-platelet clots in other parts of the circulatory system may be partially prevented through the use of anticoagulants, such as heparin. Unfortunately, heparin has not been found to be universally effective in preventing reocclusion in myocardial infarction victims in which the degree of blood vessel occlusion is greater than or equal to 70%, particularly in those patients with severe residual coronary stenosis. Among the more promising of the agents are hirudin and its analogs, which bind to and inactivate thrombin. Hirudin has a theoretical advantage over heparin as an anti-thrombotic agent. Thrombin bound to thrombi or platelets is relatively protected from inhibition by heparin while hirudin, at least in vitro, is still effective. Other promising investigational agents include fibrinogen receptor antagonists, which block platelet aggregation and dense granule release by a mechanism distinct from that of aspirin, and inhibitors of thromboxane production.

There is therefore a need for additional antithrombin agents which exhibit low toxicity, little or no antigenicity, and a very short clearance time from circulation.

SUMMARY OF THE INVENTION

Isolated proteins with antithrombin activity and nucleotide sequences encoding the proteins are provided. The protein named thrombostasin is isolated from the salivary glands of *Haematobia irritans*, the blood-feeding horn fly. The provided proteins and nucleotides are particularly useful as veterinary vaccines in prevention of blood-feeding in cattle by the infesting horn fly.

The proteins of the invention are also useful in treatment of thrombosis.

Methods of administering the proteins and nucleotide sequences of the invention are also provided.

BRIEF DESCRIPTION OF THE DRAWINGS

FIGS. 5A, 5B, and 5C show HPLC purification of active salivary thrombostasin.

DETAILED DESCRIPTION OF THE INVENTION

Figure 1:
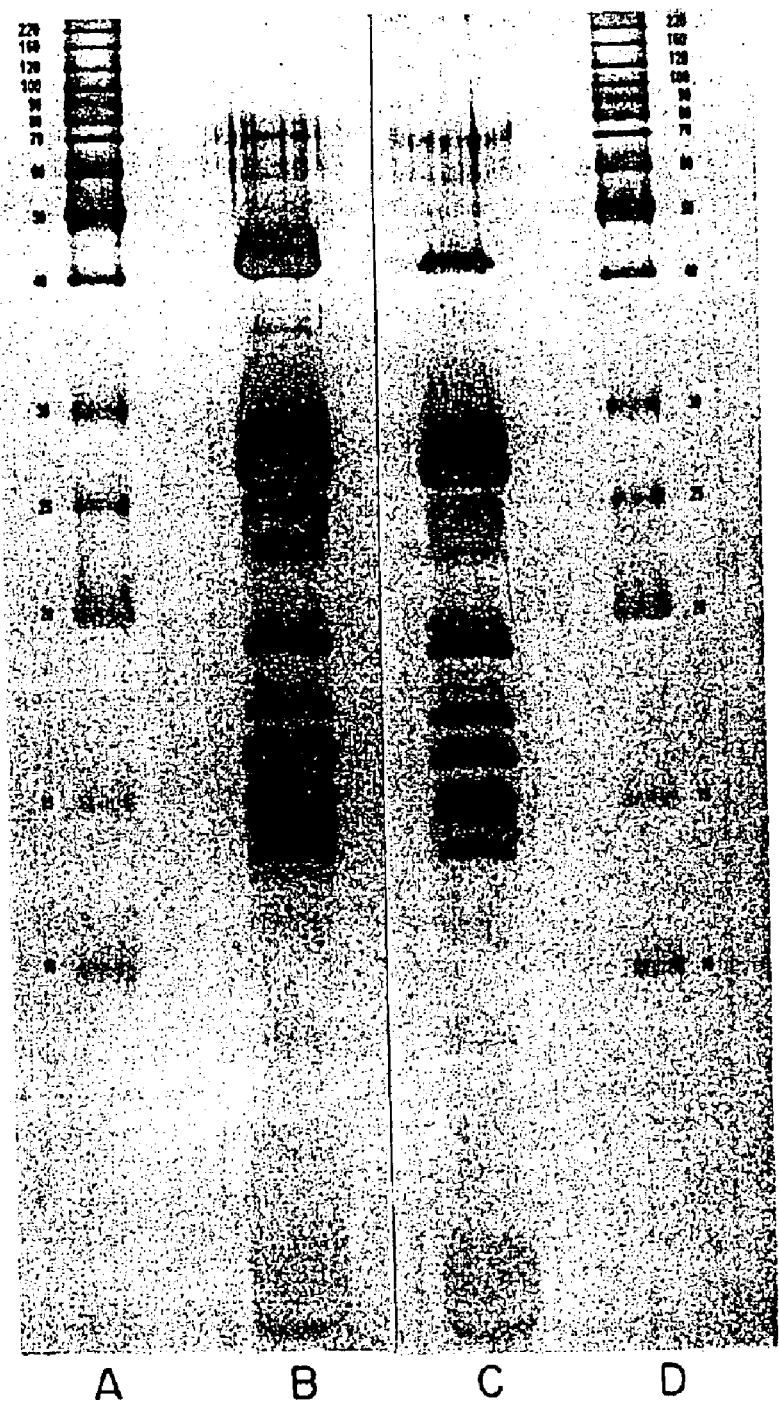
FIG. 1 shows molecular weight comparison of proteins in colony-versus field collected flies by relative mobility on SDS PAGE.

Methods and compositions for preventing hematophagy (blood-feeding) in cattle, and treatment of thrombosis in a mammal are provided. The compositions comprise protein from the salivary gland of the hematophagous horn fly *Haematobia irritans* which, as described in Yeates et al. (1999) *Annu. Rev. Entemol.* 44: 397–428, belong to the suborder Cyclorrhapha of the order Diptera. Nucleotide sequences encoding the antithrombin protein are additionally provided. The protein has been designated thrombostasin. The major function of the protein is to prevent coagulation by inhibiting the activity of thrombin (factor II).

By "hematophagy" is intended feeding on the blood of a host organism by another organism. By "hematophagous infestation" is intended a host-parasite relationship comprising feeding on the blood of the host by the parasite. By "thrombosis" is intended the formation, development or presence of a thrombus. By "antithrombin activity" is intended a biological activity that reduces or eliminates the procoagulant action of thrombin; and/or inhibits thrombosis.

It is recognized that methods are available in the art to obtain the complete coding sequence for the antithrombin protein of the invention. Such methods are disclosed for example in Sambrook et al. (1989) *Molecular Cloning: A Laboratory Manual* (Cold Spring Harbor Laboratory Press, Plainview, N.Y.).

Substantially purified preparations of thrombostasin are provided. Such substantially purified preparations include proteins substantially free of any compound normally associated with the protein in its natural state. Such proteins can be assessed for purity by SDS-PAGE, chromatography, electrophoresis or other methods. See, M. P. Deutscher (ed.), *Guide to Protein Purification*, Academic Press, Inc. (1990).

The terms "substantially pure" or "substantially purified" are not meant to exclude artificial or synthetic mixtures of the protein with other compounds. It is recognized that the antithrombin proteins of the present invention include those proteins homologous to, and having essentially the same biological properties as, the antithrombin protein described herein, and particularly the protein disclosed herein in SEQ ID NO: 2, SEQ ID NO:5, or SEQ ID NO:7. This definition is intended to encompass natural allelic variations in the genes. It is also recognized that "substantially purified" proteins of the present invention as described herein can be of other species of origin, including but not limited to other species of the suborder Cyclorrhapha.

The invention also provides fragments of the antithrombin protein and nucleotide sequence disclosed in SEQ ID NOs: 1, 2, 4, 5, 6, and 7. Fragments of the protein may range in size from at least 10, 20, 30 or more amino acids. Such fragments may retain biological activity or comprise active regions of the protein.

Polynucleotide fragments may also range in size from at least 15, 20, 30 or more contiguous nucleotides. The sequences find use as hybridization process or molecular markers.

Such fragments can be readily made by chemical methods including commercially available automated methods or by recombinant DNA methods known to the ordinarily skilled artisan, and described below. It is recognized that biological functions of anti-hemostasis, including those related to antithrombin anticoagulant activity and/or modulation of immune response may be carried out by the described fragments.

The invention additionally encompasses the nucleotide sequences which encode the proteins of the invention. The nucleotide sequence of the PCR-cloned coding sequence from *H. irritans* is provided in SEQ ID NO: 1; however, it is recognized that cloned genes of the present invention can be of other species of origin, including but not limited to other species of the suborder Cyclorrhapha.

DNAs which hybridize to the nucleotide sequence of the antithrombin gene from the horn fly are also an aspect of this invention. Conditions, which will permit other DNAs to hybridize to the DNA disclosed herein, can be determined in accordance with known techniques. For example, hybridization of such sequences may be carried out under conditions of reduced stringency, medium stringency or even stringent conditions (e.g., conditions represented by a wash stringency of 35–40% Formamide with 5× Denhardt's solution, 0.5% SDS and 1×SSPE at 37° C.; conditions represented by a wash stringency of 40–45% Formamide with 5×Denhardt's solution, 0.5% SDS, and 1× SSPE at 42EC; and conditions represented by a wash stringency of 50% Formamide with 5× Denhardt's solution, 0.5% SDS and 1×SSPE at 42EC, respectively, to DNA encoding the genes disclosed herein in a standard hybridization assay. See J. Sambrook et al. (1989) *Molecular Cloning: A Laboratory Manual* ($2^{nd}$ ed.) (Cold Spring Harbor Laboratory).

In general, sequences which code for the antithrombin protein and hybridize to the nucleotide sequence disclosed herein will be at least 40% homologous, about 60% to 70% homologous, and even about 80%, 85%, 90% homologous or more with the disclosed sequences. Such sequences are substantially homologous to the nucleotide sequences disclosed herein and encompassed by the invention. Further, the amino acid sequences of the antithrombin proteins isolated by hybridization to the DNA's disclosed herein are also an aspect of this invention. The degeneracy of the genetic code, which allows different nucleic acid sequences to code for the same protein or peptide, is well known in the literature. See, e.g., U.S. Pat. No. 4,757,006.

The hybridization probes may be cDNA fragments or oligonucleotides, and may be labeled with a detectable group as known in the art. Pairs of probes which will serve as PCR primers for the antithrombin gene or a protein thereof may be used in accordance with the process described in U.S. Pat. Nos. 4,683,202 and 4,683,195.

The polypeptides of the invention may be subject to one or more post-translational modifications such as sulphation, COOH-amidation, acylation or chemical alteration of the polypeptide chain.

It is recognized that the nucleotide and peptide sequences of the invention may be altered in various ways including amino acid substitutions, deletions, truncations, and insertions. Methods for such manipulations are generally known in the art. For example, amino acid sequence variants of the peptides and proteins can be prepared by mutations in the DNA. Methods for mutagenesis and nucleotide sequence alterations are well known in the art. See, for example, Kunkel, T. (1985) *Proc. Natl. Acad. Sci. U.S.A* 82:488–492; Kunkel et al. (1987) *Methods in Enzymol.* 154:367–382; U.S. Pat. No. 4,873,192; Walker and Gaastra (eds.) *Techniques in Molecular Biology*, MacMillan Publishing Company, NY (1983) and the references cited therein. Thus, the nucleotide sequences of the invention include both the naturally occurring sequences as well as mutant. Likewise, the peptides and proteins of the invention encompass both naturally occurring and modified forms thereof. Such variants will continue to possess the desired activity. It is recognized that the mutations that will be made in the DNA encoding the variant must not place the sequence out of reading frame and preferably will not create sequences deleterious to expression of the gene product. See, EP Patent Application, Publication No. 75,444.

The proteins of the invention include the naturally occurring forms as well as variants thereof. These variants will be substantially homologous and functionally equivalent to the native protein. As used herein, two proteins (or a region of the proteins) are "substantially homologous" when the amino acid sequences are typically at least about 40%, more typically at least about 60%–70%, and most typically at least about 80%, 85%, 90% or more identical. A substantially homologous amino acid sequence, according to the present invention, will be encoded by a nucleic acid sequence hybridizing to the nucleic acid sequence, or portion thereof, of the nucleotide sequence shown in SEQ ID NO:1, SEQ ID NO:4, SEQ ID NO:6, or otherwise described herein under stringent conditions as more fully described below.

Thus, a variant of a native protein is "substantially homologous" to the native protein when at least about 40%, more preferably at least about 60%–70%, and most preferably at least about 80%, 85%, 90%, or more of its amino acid sequence is identical to the amino acid sequence of the native protein. A variant may differ by as few as 1, 2, 3, or 4 amino acids. A variant polypeptide can differ in amino acid sequence by one or more substitutions, deletions, insertions, inversions, fusions, and truncations or a combination of any of these.

By "functionally equivalent" is intended that the sequence of the variant defines a chain that produces a protein having substantially the same biological activity as the native protein of interest. Such functionally equivalent variants that comprise substantial sequence variations are also encompassed by the invention. Thus a functionally equivalent variant of the native protein will have a sufficient biological activity to be therapeutically useful. By therapeutically useful is intended effective in achieving a therapeutic goal as discussed below.

Methods are available in the art for determining functional equivalence. Biological activity can be measured using assays specifically designed for measuring activity of the native protein, including assays described in the present invention. Additionally, antibodies raised against the biologically active native protein can be tested for their ability to bind to the functionally equivalent variant, where effective binding is indicative of a protein having conformation similar to that of the native protein.

Variant polypeptides can be fully functional or can lack function in one or more activities. Thus, in the present case, variations can affect the function, for example, of one or more of the modules, domains, or functional subregions of the proteins and polypeptides of the invention.

Fully functional variants typically contain only conservative variation or variation in non-critical residues or in non-critical regions. Functional variants can also contain substitution of similar amino acids, which result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region. As indicated, variants can be naturally-occurring or can be made by recombinant means or chemical synthesis to provide useful and novel characteristics for the polypeptide.

Amino acids that are essential for function can be identified by methods known in the art, such as site-directed mutagenesis or alanine-scanning mutagenesis (Cunningham et al., *Science* 244:1081–1085 (1989)). The latter procedure introduces single alanine mutations at every residue in the molecule. The resulting mutant molecules are then tested for biological activity. Sites that are critical can also be determined by structural analysis such as crystallization, nuclear magnetic resonance or photoaffinity labeling (Smith et al., *J. Mol. Biol.* 224:899–904 (1992); de Vos et al. *Science* 255:306–312 (1992)).

The invention further encompasses variant polynucleotides, and fragments thereof, that differ from the nucleotide sequence shown in SEQ ID NO:1, SEQ ID NO:4, or SEQ ID NO:6, or otherwise described herein, due to degeneracy of the genetic code and thus encode the same protein as that encoded by the nucleotide sequence shown in SEQ ID NO:1, SEQ ID NO:4, or SEQ ID NO:6 or otherwise described herein.

The invention also provides nucleic acid molecules encoding the variant polypeptides described herein. Such polynucleotides may be naturally occurring, such as allelic variants (same locus), homologs (different locus), and orthologs (different organism), or may be constructed by recombinant DNA methods or by chemical synthesis. Such non-naturally occurring variants may be made by mutagenesis techniques, including those applied to polynucleotides, cells, or organisms. Accordingly, as discussed above, the variants can contain nucleotide substitutions, deletions, inversions and insertions.

Variation can occur in either or both the coding and non-coding regions. The variations can produce both conservative and non-conservative amino acid substitutions.

Orthologs, homologs, and allelic variants can be identified using methods well known in the art. These variants comprise a nucleotide sequence encoding a protein that is at least typically about 40%, more typically at least about 60%–70%, and most typically at least about 80%, 85%, 90% or more homologous to the nucleotide sequence shown in SEQ ID NO:1, SEQ ID NO:4, SEQ ID NO: 6 or otherwise described herein, or a fragment of this sequence. Such nucleic acid molecules can readily be identified as being able to hybridize under stringent conditions, to the nucleotide sequence shown in SEQ ID NO:1, SEQ ID NO:4, SEQ ID NO: 6 or otherwise described herein, or a fragment of the sequence. It is understood that stringent hybridization does not indicate substantial homology where it is due to general homology, such as poly A sequences, or sequences common to all or most proteins in an organism or class of proteins.

To determine the percent homology of two amino acid sequences, or of two nucleotide sequences, the sequences are aligned for optimal comparison purposes (e.g., gaps can be introduced in the sequence of one protein or nucleic acid for optimal alignment with the other protein or nucleic acid). The amino acid residues or nucleotides at corresponding amino acid positions or nucleotide positions are then compared. When a position in one sequence is occupied by the same amino acid residue or nucleotide as the corresponding position in the other sequence, then the molecules are homologous at that position. As used herein, amino acid or nucleic acid "homology" is equivalent to amino acid or nucleic acid "identity". The percent homology between the two sequences is a function of the number of identical positions shared by the sequences (i.e., percent homology equals the number of identical positions/total number of positions times 100).

The invention also encompasses proteins or polypeptides having a lower degree of identity but having sufficient similarity so as to perform one or more of the same functions performed by the antithrombin proteins described herein. Similarity is determined by conserved amino acid substitution. Such substitutits are those that substitute the given amino acid in a polypeptide by another amino acid of like characteristics. Conservative substitutions are likely to be phenotypically silent. Guidance concerning which amino acid changes are likely to be phenotypically silent are found in Bowie et al., *Science* 247:1306–1310 (1990).

Both identity and similarity can be readily calculated (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data, Part* 1, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). Preferred computer program methods to determine identify and similarity between two sequences include, but are not limited to, GCG program package (Devereux, J. (1984) *Nuc. Acids Res.* 12(1):387), BLASTP, BLASTN, and FASTA (Atschul, S. F. (1990) *J. Molec. Biol.* 215:403); utilizing the default parameters available within the programs. By substantial sequence similarity, identity or homology is intended sequences having at least about 60%, 70%, 75%, 80%, 85%, 90%, 95% or more similarity.

DNA sequences can also be synthesized chemically or modified by site-directed mutagenesis to reflect the codon preference of the host cell and increase the expression efficiency.

The proteins of the invention can be engineered in accordance with the present invention by chemical methods or molecular biology techniques. Molecular biology methods are most convenient since proteins can be engineered by manipulating the DNA sequences encoding them. Genomic DNA, cDNA, synthetic DNA, and any combination thereof may be used for this purpose. Genomic DNA sequences or cDNA sequences encoding proteins can be isolated based on the amino acid sequence of proteins or certain protein properties. Many methods of sequence isolation are known in the art of molecular biology. See particularly Sambrook et al. (1989) *Molecular Cloning: A Laboratory Manual* (Cold Spring Harbor Laboratory Press, Plainview, N.Y.), herein incorporated by reference.

To produce an antithrombin polypeptide by recombinant DNA technology, a gene encoding a polypeptide of the invention is prepared. The DNA coding sequence typically does not contain introns. The DNA sequence is isolated and purified, the gene is inserted in an expression vector able to drive expression and production of the recombinant product. The DNA sequence may be a cDNA sequence, or alternatively a synthetic DNA sequence. A synthetic gene is typically prepared by chemically synthesizing oligonucleotides that, in total, correspond to the desired gene. The synthesized oligonucleotides are then assembled to obtain the gene.

If desired, the gene sequence may be modified by site-directed mutagenesis to introduce one or more coding changes. Typically, a gene is constructed with restriction sites at each end to facilitate its subsequent manipulation.

The DNA sequence may be constructed to comprise a leader peptide. The leader peptide is capable of directing secretion of the polypeptide from cells in which the polypeptide is to be expressed. The sequence encoding the leader peptide is typically fused to the 5'-end of the DNA sequence encoding the polypeptide. Leader sequences are known in the art and include the OmpA leader peptide, the leader peptide of vesicular stomatitis virus G protein (VSV G protein). The OmpA leader is useful when expression is in a bacterial host, such as *E. coli* while the VSVG protein is useful when expression is in insect cells.

The DNA sequence may be constructed to comprise a cleavable site to release the polypeptide of the invention. A DNA sequence may be used which encodes a carrier polypeptide sequence fused via a cleavable linkage to the N-terminus of a polypeptide of the invention. The cleavable linkage may be one cleavable by cyanogen bromide.

For expression of the polypeptides, an expression vector is constructed which comprises a DNA sequence encoding the polypeptide which is capable of expressing the polypeptide in a suitable host. Appropriate transcriptional and translational control elements are provided, including a promoter for the DNA sequence, a transcriptional termination site, and translation start and stop codons. The DNA sequence is provided in the correct frame such as to enable expression of the polypeptide to occur in a host compatible with the vector.

The expression vector typically comprises an origin of replication and, if desired, a selectable marker gene such as antibiotic resistance. The expression vector may be a plasmid, a virus, particularly a baculovirus, and the like.

Once the nucleotide sequences encoding the antithrombin proteins of the invention have been isolated, they can be manipulated and used to express the protein in a variety of hosts including other organisms, including microorganisms.

Once the nucleotide sequence is identified and known, those skilled in the art can produce large quantities of the protein for therapeutic use. Accordingly, recombinant protein and methods for producing the recombinant protein are encompassed by the present invention. In this manner, the nucleotide sequence encoding the antithrombin protein can be utilized in vectors for expression in various types of host cells, including both procaryotes and eucaryotes, to produce large quantities of the protein, or active analogues, or fragments thereof, and other constructs having antithrombin activity.

Generally, methods for the expression of recombinant DNA are known in the art. See, for example, Sambrook et al. (1989) *Molecular Cloning*, Cold Spring Harbor Laboratory. Additionally, host cells and expression vectors, such as the baculovirus expression described in U.S. Pat. Nos. 4,745,051 and 4,879,236. In general, a baculovirus expression vector comprises a baculovirus genome containing the gene to be expressed inserted into the polyhedron gene at a position ranging from the polyhedron transcriptional start signal to the ATG start site and under the transcriptional control of a baculovirus polyhedron promoter.

A broad variety of suitable procaryotic and microbial vectors are available. Likewise, the promoters and other regulatory agents used in expression of foreign proteins are available in the art. Promoters commonly used in recombinant microbial expression vectors are known in the art and include the beta-lictamase (penicillinase) and lactose promoter systems (Chang et al. (1978) *Nature* 275:615 and Goeddel et al. (1979) *Nature* 281:544); A tryptophan (TRP) promoter system (Goeddel et al. (1980) *Nucleic Acids Res.* 8:4057 and the EPO Application Publication No. 36,776); and the Tac promoter (DeBoer et al. (1983) *Proc. Natl. Acad. Sci. U.S.A*, 80:21). While these are commonly used, other microbial promoters are available. Details concerning nucleotide sequences of many have been published, enabling a skilled worker to operably ligate them to DNA encoding the protein in plasmid or viral vectors. See, for example, Siedenlist et al. (1980) *Cell* 20:269.

Eucaryotic host cells such as yeast may be transformed with suitable protein-encoding vectors. See, e.g., U.S. Pat. No. 4,745,057. *Saccharomyces cerevisiae* is the most commonly used among lower eukaryotic host microorganisms, although a number of other strains are commonly available. Yeast vectors may contain an origin of replication from the 2 micron yeast plasmid or an autonomously replicating sequence (ARS), a promoter, DNA encoding the desired protein, sequences for polyadenylation and transcription termination, and a selection gene. An exemplary plasmid is YRp7, (Stinchcomb et al. (1979) *Nature* 282:9; Kingsman et al. (1979) *Gene* 7:141; Tschemper et al. (1980) *Gene* 10:157). This plasmid contains the trp1 gene, which provides a selection marker for a mutant strain of yeast lacking the ability to grow in tryptophan, for example ATCC No. 44076 or PEP4-1 (Jones (1977) *Genetics* 85:12). The presence of the trp1 lesion in the yeast host cell genome then provides an effective environment for detecting transformation by growth in the absence of tryptophan.

Suitable promoter sequences for use in yeast vectors include the promoters for metallothionein, alcohol dehydrogenase, adenylate cyclase, 3-phosphoglycerate kinase (Hitzeman et al. (1980) *J. Biol. Chem.* 255:2073) and other glycolytic enzymes (Hess et al. (1968) *J. Adv. Enzyme Reg.* 7:149; and Holland et al. (1978) *Biochemistry* 17:4900) such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Suitable vectors and promoters for use in yeast expression are further described in R. Hitzeman et al. EPO Publn. No. 73,657.

The invention provides antibody preparations that selectively bind the proteins of the invention, or any variants or fragments thereof as described. An antibody is considered to selectively bind, even if it also binds to other proteins that are not substantially homologous with the antithrombin protein. These other proteins share homology with a fragment or domain of the antithrombin protein giving rise to antibodies that bind to both proteins by virtue of the homologous sequence. In this aspect, it is recognized that antibody binding to the antithrombin protein is still selective.

The preparations encompass monoclonal or polyclonal antibodies, intact antibodies or fragments thereof (e.g. Fab), purified preparations such as affinity-purified preparations, or less pure preparations such as ascites fluid, sera and the like. Methods for raising antibodies are well known in the art and include but are not limited to those described in Harlow and Lane ((1988) Antibodies, A Laboratory Manual, Cold Spring Harbor Laboratory Press), the contents of which are herein incorporated by reference. The invention also embodies antibody preparations which neutralize biological functions of the provided proteins, variants or fragments thereof. Such functions include but are not limited to antithrombin activity. The invention also provides compositions capable of modulating the immune response. By modulating the immune response is intended a determinable change in the immune system of a host organism effected by administering the herein described compositions of the invention to that host. Working examples of such modulation of immune response, as well as methods of making and assessing selectivity of antibody preparations are provided in the Experimental section of this application, and are herein incorporated by reference.

The compositions of the present invention find therapeutic use as veterinary vaccines in treatment of hematophagy in a mammal. The methods comprise administering to the mammal a veterinary vaccine comprising a therapeutically effective amount of the compositions of the invention. In this aspect, a therapeutically effective amount is intended as that amount which effects a determinable reduction, amelioration, elimination or prevention of hematophagous infestation in the mammal to which the vaccine of the present invention was administered. While the vaccines of the invention can be used with any mammal, of particular interest are livestock, more particularly, horses, cattle, and the like. The compositions are useful for vaccination against the hematophagous fly of the suborder Cyclorrhapha, more particularly of the species *Haematobia irritans*, even more particularly of the subspecies irritans or exigua. However, the invention vaccination against any hematophagous organism where such vaccination using compositions and methods of the present invention is therapeutically effective.

For veterinary applications, the compositions of the invention can be formulated into any acceptable pharmaceutical preparation as described below or any other acceptable preparation for veterinary use. In one embodiment of the invention, the vaccines comprise therapeutically effective amounts of the proteins of the invention, or any variant or fragment thereof as described herein.

In a preferred embodiment, the vaccines comprise the nucleotide compositions of the invention as described herein. As described by Cox et al. (1993) *J. Virol.* 67:5664–5667; Fynan et al. (1993) *Proc. Natl. Acad. Sci. USA* 90:11478–11482; and Lewis et al. (1997) *Vaccine* 15:861–864; and reviewed by Robinson (1997) *Vaccine* 15:785–787; and Tighe et al. (1998) *Immunol. Today* 19:89–97, the contents of all of which are herein incorporated by reference, nucleic acid vaccines can be readily constructed and produced. In general, target DNA sequences encoding the protein to be used as an immunogen are cloned into eukaryotic expression vectors. The constructed plasmid is grown in bacteria and purified. The purified plasmid DNA is then directly injected into the animal generally by intramuscular injection, but also by intradermal injection; where its expression by cells in the inoculated host produces the target protein, thereby raising an immune response. See, for example, Cox et al. (1993) *J. Virol.* 67:5664–5667, herein incorporated by reference. Nanogram levels of DNA-expressed protein may be utilized to stimulate an immune response and protect against infectious agents achieved by skin, muscle and intravenous inoculations of DNA. See, for example, Fynan et al. (1993) *Proc. Natl. Acad. Sci. USA* 90:11478–11482; Cox et al. (1993) *J. Virol.* 67:5664–5667, herein incorporated by reference. Such plasmids introduced by intramuscular or intradermal injection stimulate a protective response that abrogates clinical disease following challenge.

The compositions of the present invention can be formulated into pharmaceutical preparations for therapeutic use as antithrombin agents. Such compositions find use in the treatment of venous thrombosis, vascular shunt occlusion and thrombin-included disseminated intravascular coagulation.

The compositions of the invention can be used alone or in combination with other antithrombin and therapeutic agents including veterinary agents such as vaccines. Other agents are known in the art.

The antithrombin compositions can be formulated according to known methods to prepare pharmaceutically useful compositions, such as by admixture with a pharmaceutically acceptable carrier vehicle. Suitable vehicles and their formulation are described, for example, in Remington's Pharmaceutical Sciences 19th ed., Osol, A. (ed.), Mack Easton Pa. (1980). In order to form a pharmaceutically acceptable composition suitable for effective administration, such compositions will contain an effective amount of the antithrombin protein, either alone, or with a suitable amount of carrier vehicle.

Additional pharmaceutical methods may be employed to control the duration of action. Controlled release preparations may be achieved by the use of polymers to complex or absorb the compositions. The controlled delivery may be exercised by selecting appropriate macromolecules (for example, polyesters, polyamino acids, polyvinyl pyrrolidone, ethylene-vinylacetate, methylcellulose, carbosymethylcellulose, or protamine sulfate). The rate of drug release may also be controlled by altering the concentration of such macromolecules.

Another possible method for controlling the duration of action comprises incorporating the therapeutic agents into particles of a polymeric substance such as polyesters, polyamino acids, hydrogels, poly(lactic acid) or ethylene vinylacetate copolymers. Alternatively, it is possible to entrap the therapeutic agents in microcapsules prepared, for example, by coacervation techniques or by interfacial polymerization, for example, by the use of hydroxymethyl cellulose or gelatin-microcapsules or poly (methylmethacrylate) microcapsules, respectively, or in a colloid drug delivery system, for example, liposomes, albumin, microspheres, microemulsions, nanoparticles, nanocapsules, or in macroemulsions. Such teachings are disclosed in Remington's Pharmaceutical Sciences (1980).

In more specific embodiments, a polypeptide of the invention may be converted into a pharmaceutically acceptable salt. It may be converted into an acid additional salt with an organic or inorganic acid. Suitable acids include acetic, succinic and hydrochloric acid. Alternatively, the peptide may be converted into a carboxylic acid salt such as the ammonium salt or an alkali metal salt such as the sodium or potassium salt.

A polypeptide or pharmaceutically acceptable salt thereof may be used in a pharmaceutical composition, together with a pharmaceutically acceptable carrier or excipient therefore. Such a formulation is typically for intravenous administration (in which case the carrier is generally sterile saline or water of acceptable purity). A polypeptide can therefore be used for the therapy and prophylaxis of thrombosis and thromboembolisms in a human or other mammal, including the prophylaxis of post-operative thrombosis, for acute shock therapy (for example for septic or polytraumatic shock), for the therapy of consumption coagulopathics, in hemodialyses, haemoseparations and in extracorporeal blood circulation. In one embodiment of the invention, the polypeptide or salt thereof can be coadministered with a plasminogen activator, such as tissue plasminogen activator.

The dosage depends especially on the specific form of administration and on the purpose of the therapy or prophylaxis. The size of the individual doses and the administration regime can best be determined by way of an individual judgment of the particular case of illness; the methods of determining relevant blood factors required for this purpose are familiar to the person skilled in the art. Normally, in the case of an injection the therapeutically effective amount of the compounds according to the invention is in a dosage range of from approximately from 0.005 or 0.01 to approximately 0.05 or 0.1 mg/kg body weight, preferably from approximately 0.01 to approximately 0.05 mg/kg body weight.

The administration is effected by intravenous, intramuscular or subcutaneous injection. Accordingly, pharmaceutical compositions for parenteral administration in single dose form contain per dose, depending on the mode of administration, from approximately 0.4 to approximately 7.5 mg of the compound according to the invention. In addition to the active ingredient these pharmaceutical compositions usually also contain a buffer, for example a phosphate buffer, which is intended to keep the pH value between approximately 3.5 and 7, and also sodium chloride, mannitol or sorbitol for adjusting the isotonicity. The preparations may be freeze-dried or dissolved. An antibacterially active preservative may be included, for example from 0.2 to 0.3% 4-hydroxybenzoic acid methyl ester or ethyl ester.

A composition for topical application can be in the form of an aqueous solution, lotion or gel, an oily solution or suspension or a fat-containing or, especially, emulsified ointment. A composition in the form of an aqueous solution is obtained, for example, by dissolving the active ingredients according to the invention, or a therapeutically acceptable salt thereof, in an aqueous buffer solution of from e.g., pH 4 to pH 6.5 and, if desired, adding a further active ingredient, for example an anti-inflammatory agent, and/or a polymeric binder, for example polyvinylpyrrolidone, and/or a preservative. The concentration of active ingredients is from approximately 0.1 to approximately 1.5 mg, preferably from 0.25 to 1.0 mg, in 10 ml of a solution or 10 g of a gel.

An oily form of administration for topical application is obtained, for example, by suspending the active ingredient according to the invention, or a therapeutically acceptable salt thereof, in an oil, optionally with the addition of swelling agents, such as aluminum stearate, and/or surfactants (tensides) having an HLB value ("hydrophilic-lipophilic balance") of below 10, such as fatty acid monomers of polyhydric alcohols, for example glycerin monostearate, sorbitan monolaurate, sorbitan monostearate or sorbitan monooleate. A fat-containing ointment is obtained, for example, by suspending the active ingredient according to the invention, or a salt thereof, in a spreadable fatty base, optionally with the addition of a tenside having an HLB value of below 10. An emulsified ointment is obtained by triturating an aqueous solution of the active ingredient according to the invention, or a salt thereof, in a soft, spreadable fatty base with the addition of a tenside having an HLB value of below 10. All these forms for topical application can also contain preservatives. The concentration of active ingredient is from approximately 0.1 to approximately 1.5 mg, preferably from 0.25 to 1.0 mg, in approximately 10 g of base.

In addition to the compositions described above and pharmaceutical compositions analogous thereto that are intended for direct medicinal use in the body of a human or a mammal, the present invention relates also to pharmaceutical compositions and preparations for medicinal use outside the living body of humans or mammals. Such compositions and preparations are used especially as anticoagulant additives to blood that is being subjected to circulation or treatment outside the body (for example haemoseparation). Such preparations, such as stock solutions or alternatively preparations in single dose form, are similar in composition to the injection preparations described above; however, the amount of concentration of active ingredient is advantageously based on the volume of blood to be treated or, more precisely, on its thrombin content. Depending on the specific purpose, the suitable dose is from approximately 0.01 to approximately 1.0 mg of the active ingredient/liter of blood, although the upper limit may still be exceeded without risk as the agent is harmless even in relatively high amounts.

Experimental

Collection and Rearing of H. irritans

Pupae were shipped from the U.S.D.A. Livestock Insects Research Laboratory in Kerrville, Tex., on a biweekly basis and stored at 4° C. until needed. They were removed and placed in stainless steel cages (18"×18"×18") at room temperature (21–22° C.) with 16:8 hours (L:D) to promote emergence of adults. An absorbent cotton pad was placed on top of each cage and used as a wick to supply fresh blood to adults on a daily basis.

Wild-caught adults collected from the University of Arizona dairy herd and from the Auburn University beef and dairy herds were used for some assays. They were transported to the laboratory within an hour of collection and maintained as above prior to experimentation.

Recovery of Salivary Glands

Both sexes of H. irritans are obligate blood feeders and their salivary glands are similar in morphology and location in the body to stable flies (Stomoxys calcitrans) and tsetse flies (Glossina spp.) The following protocol was used for dissection of glands: (a) the fly was "knocked down" with humidified $CO_2$, passed briefly through a 70% ethanol (ETOH) bath, and then rinsed in deionized water; (b) it was placed on a clean glass slide in a drop of chilled 0.15M saline and the legs, wings and head were removed. The thorax was split sagittally using a razor blade or scalpel; (c) the fly was then transferred to a fresh drop of chilled saline in a watch glass or a small dish filled with paraffin. Using minute dissecting needles, the two halves of the thorax were then peeled back; (d) using forceps, the abdominal cuticle was pulled away, exposing the internal organs. The salivary glands were then teased away from the gut tissue. The anterior end of the gut (the cardia) was clipped and then gut-salivary gland assembly withdrawn by pulling it through the abdomen-thorax constriction; (e) the glands were then teased away from the gut, rinsed once in cold saline and transferred to an Eppendorf® tube to be kept in ice for collection, and then frozen at −70° C.

Preparation of Salivary Gland Extracts

Salivary gland extracts (SGEs) were prepared as described by Cupp et al. (1993) J. Insect Physiol. 39:817–821, or by sonication. For the former method, glands were homogenized in a 1:1 mixture of 0.15 M NaCl solution and 0.1% Triton X-100 was added to the thawed sample, which was then refrozen. Extracts were prepared by thawing the solubilized sample, vortexing it for 30 seconds and then centrifuging it at 14,000×g for 30 seconds at 4° C. For the latter method, sonic disruption of glands was obtained using 70% cycle and 70% power output of a Sonifier® 450 sonication instrument (Branson Ultrasonics, Danbury, Conn.) for 2 minutes. Eppendorf® tubes with glands were thawed and the contents disrupted by holding the tip of each tube to the base of the sonic probe immersed in an ice bath to disperse heat. Salivary gland extracts were transferred to a new tube following removal of cell fragments by centrifugation at ≈12,000×g for 5 minutes at 4° C. The amount of protein per individual gland was determined using a BCA protein assay kit (Pierce® Biotechnology. Inc., Rockford, Ill.). Initial measurement of soluble protein obtained from sonicated H. irritans salivary glands was 0.54±0.09 µg/pair of glands for females and 0.63±0.02 µg/pair of glands for males.

Collection of Saliva

To determine antihemostatic activity attributable specifically to salivary secretion, two methods were joined which have been used previously for the buffalo fly (Kerlin and Hughes (1992) Med. Vet. Entomol. 6:121–126) and mosquitoes (Hurlbut (1966) Am. J. Trop. Med. Hyg. 15:989–993) to collect saliva from these insects. Adult flies, held at room temperature, were starved for 24 hours to insure that secretions were retained in the salivary glands and that all gut contents were digested. The latter precaution is necessary since muscoid flies often regurgitate during feeding. The flies were then anesthetized with humidified CO2 and their wings removed with microdissecting scissors. The dealated flies were then glued to applicator sticks so that their mouth parts could be positioned into a capillary tube containing mineral oil. Just prior to this step, each fly was injected with 1 µl of 80 mM serotonin. The fly's proboscis was then inserted into the oil which, because of its difference in viscosity with saliva, served as a collecting medium for the serotonin-induced secretions. Salivation usually began within 30–60 seconds and the saliva could be easily seen as a clear aqueous droplet when it was expelled into the oil.

Gel Electrophoresis

Unless otherwise indicated, proteins were resolved on 15% polyacrylamide/SDS gels (SDS PAGE) by the method of Laemmli (1970) *Nature* 227:680–685, and visualized by silver staining (Bassam et al. (1991) *Annal. Biochem.* 196:80–83). Stained gels are scanned for densitometry analysis of band migration and staining intensity (Personal Densitometer® S.I. device, ImageQuaNT® computer software for Windows NT, Molecular Dynamics®, Inc., Sunnyvale, Calif.).

Proteins in Saliva

FIG. 1 depicts molecular weight comparison of proteins in saliva of colony (lane C) versus field-collected (Lane B) flies by relative mobility on SDS PAGE. Molecular weight standards in the 10–220 kDa range are shown in lanes A and D. A very similar profile is observed except for the presence of a light band at ≈36 KDa in field-collected flies. However, the concentration of proteins in the saliva of the 30 field-collected flies (B), as determined by relative intensity of staining of bands, exceeds that of corresponding bands in the saliva of 84 colony flies (C). This difference was observed routinely on silver-strained gels and indicates that field populations of *H. irritans* produce greater concentrations of salivary proteins than do flies from this colonized strain.

Apyrase Activity

Apyrase activity in SGEs was tested using a standard assay (see Cupp et al. (1993) *J. Insect Physiol.* 39:817–821). This enzyme rapidly degrades adenosine triphosphate (ATP) and adenosine diphosphate (ADP) to the monophosphate, thereby eliminating a crucial chemical signal that ordinarily promotes platelet aggregation. Extracts were prepared from wild caught male and female flies which were maintained on water for 48 hrs prior to dissection. Activity in this enzyme in SGEs was marginally detectable in *H. irritans* (2.59±0.21 milliUnits/pair of salivary gland equivalents). This lack of apyrase activity was also confirmed by the inability of *H. irritans* saliva to affect ADP-induced aggregation of platelets in bovine platelet-rich plasma (unpublished observations). Thus, apyrase activity was eliminated as a mechanism of hematophagy by *H. irritans*.

Erythema Activity

We evaluated the potential of *H. irritans* saliva to induce erythema, using intradermal injections of SGEs or by direct feeding of male and female flies on the shaved back of a New Zealand White rabbit. As a control, we also injected Simulium vittatum SGEs which produce a persistent erythema within 15 min of intradermal delivery (Cupp et al. (1994) *Am. J. Trop. Med. Hyg.* 50:235–240). A colonized strain of *S. vittatum* served as a source of salivary gland material (Bernardo et al. (1986) *Ann. Entomol. Soc. Am.* 79:610–621). No erythema was produced by either male or female *H. irritans* saliva, whether injected as an SGE or delivered by bite. Simulium vittatum SGE produced a visible erythema within 15 minutes. Thus, erythma activity was eliminated as a mechanism of hematophagy by *H. irritans*.

Other Vasodilative Activity

Studies were conducted to detect the presence of vasodilative activity in *H. irritans* SGEs or saliva using tension measurements of rat stomach (assay for prostaglandin) and rabbit aortic strips, with and without intact endothelium (see Ribeiro et al. (1992) *Exp. Parasitol.* 74:112–116; Ribeiro et al. (1994) *J. Med. Entomol.* 31:747–753). To detect bradykinin or histamine activity in *H. irritans* SGEs, the assay followed the procedure of Webster and Prado (1970) which uses the contraction in vitro of guinea pig ileum as a direct bioassay of kinin activity. Normal responses to test substances (prostaglandin E2 for rat stomach strips and norepinephrine or acetyl choline for rabbit aortic strips) were obtained, while *H. irritans* SGE showed no vaso-activity. Initially, collections of induced saliva did show activity in the rat stomach strip assay but this was lost when methysergide maleate was included (Pertz and Eich (1992) *Navnyn Schmiedebergs Arch. Pharmacol.* 345:394–401. This substance is a known inhibitor of serotonin, the compound used to elicit salivation by the fly. The presence of activity in serotonin-induced saliva, but not in SGE, indicated that the serotonin activity in those samples was derived from the injected compound used to elicit salivation. Extraction of *H. irritans* SGE to enhance detection of prostaglandin activity confirmed the negative results of the earlier vasodilatory study. No salivary activity was detected in the guinea pig ileum assay for bradykinin or histamine. Thus, the tested vasodilative activities were eliminated as mechanisms of hematophagy by *H. irritans*. The inability of hornfly SGE to elicit vasodilation when injected intradermally into the shaved skin of NZW rabbits, in vivo, was confirmed using laser doppler perfusion imaging.

Anti-coagulant Activity

Figure 2:
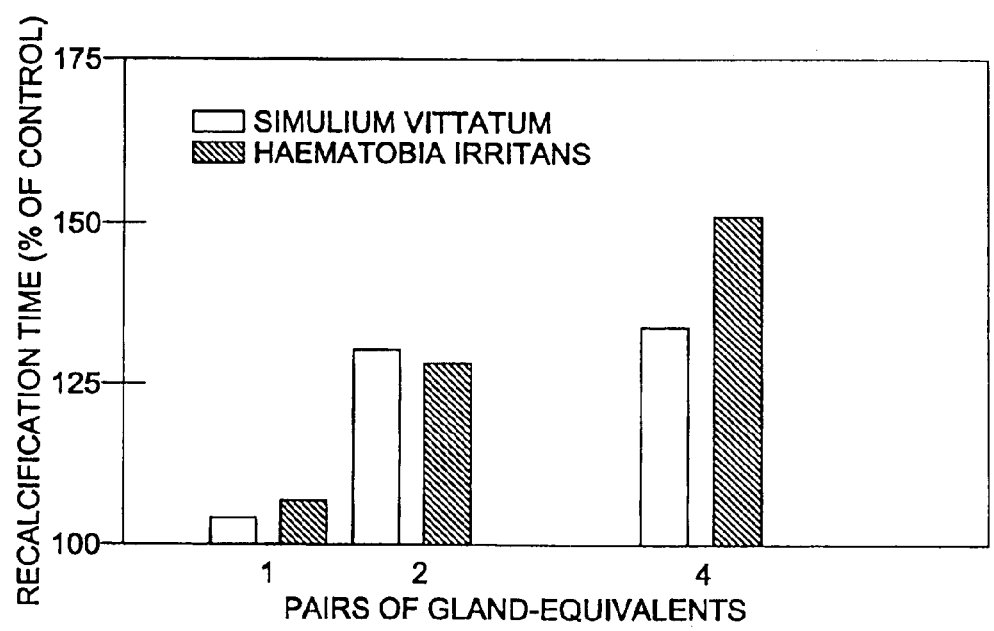
FIG. 2 depicts the recalcification time assay to test for anti coagulant activity in *H. irritans* saliva.

The re-calcification time assay was chosen to screen for anticoagulant activity, as this general assay can detect inhibitors that attack at any of the three major arms of the coagulation cascade, the extrinsic pathway, the intrinsic pathway and the final common pathway. Salivary gland extracts were prepared from both male and female *H. irritans* and from female *S. vittatum*. SGEs from the latter species were used as a positive control because the same re-calcification time assay had been used previously to detect anticoagulant activity in that species (Abebe et al. (1994) *J. Med. Entomol.* 31:908–911). Salivary gland extracts of female *H. irritans* were as potent as those of *S. vittatum* in delaying the re-calcification time of standard plasma as shown in FIG. 2. Male SGEs also delayed re-calcification time (data not shown). Comparable inhibition occurred in spite of the fact that measured protein contents were 50% lower in extracts of *H. irritans*. Thus, this anti-coagulant activity was the only anti-hemostatic activity detected for the horn fly, *H. irritans*.

Anti-hemostatic Specificity

The recalcification time assay can detect inhibition of any step in the cascade of reactions that ultimately lead to blood-clotting (coagulation), and thus it is a useful general test to screen for the presence of an unknown inhibitor. Because blood-clotting is the result of a series of reactions, horn fly saliva could delay clotting by inhibiting a specific step in the blood-clotting cascade or, alternatively, delay the normal rate of hemostasis by dissolving a clot after it was formed (fibrinolytic activity).

For analytical purposes the clotting reactions are typically grouped into three sub-pathways which are monitored by different clotting assays; i.e., the intrinsic (activated partial thromboplastin time test=APTT), the extrinsic (prothrombin time test=PTT) and the final common pathway (thrombin time=TT). Recalcification time, PTT, TT and APTT assays are well known by those ordinarily skilled in the art. For example, see Biggs et al. ((1962) *Human Blood Coagulation And Its Disorders,* 3rd ed., Blackwell Scientific Publications, Oxford) for recalcification time assays, and Turgeon M. L. ((1993) Clinical Hematology. Theory and Procedures, 2nd ed., Little, Brown and Company, Boston) for APTT, PTT and TT assays. APTT II is a modification of the APTT I test and is more sensitive.

Using these tests, several properties of horn fly anticlotting activity were determined as shown in Table 1:1) Horn fly salivary gland extracts or saliva caused delay in clotting of all the tests, indicating that at least one inhibitor is present that works in the final common pathway, i.e. after the formation of thrombin from prothrombin. 2) Saliva from wild-type flies contains more inhibitor activity than saliva collected from the same number of colony flies. 3) Inhibitor activity in colony flies held for 48 hours after emergence is greater than at 24 hours post-emergence.

TABLE 1

Delay in blood clotting by *Haematobia irritans* salivary gland extracts (SGE) or serotonin-induced saliva.

| Source | # flies | Type of Assay | % of Control* |
|---|---|---|---|
| SGE-colony | 1 | Recalcification | 106 |
| SGE-colony | 2 | Recalcification | 128 |
| Saliva-colony (24 h) | 4 | Recalcification | 143 |
| Saliva-colony (48 h) | 4 | Recalcification | 175 |
| Saliva-wild type | 1 | Recalcification | 127 |
| Saliva-wild type | 2 | Recalcification | 161 |
| SGE-colony | 1 | APTT-I | 113 |
| SGE-colony | 2 | APTT-I | 149 |
| Saliva-colony | 1 | APTT-I | 112 |
| SGE-colony | 1 | APTT-II | 144 |
| Saliva-wild type | 1 | APTT-II | 210 |
| SGE-colony | 1 | PTT | 120 |
| SGE-colony | 2 | PTT | 140 |
| Saliva-wild type | 1 | PTT | 156 |
| SGE-colony | 1 | TT | ND |
| SGE-colony | 2 | TT | 109 |
| Saliva-wild type | 1 | TT | 158 |

ND not determined
*Each value is the mean of 4 assays

Figure 3:
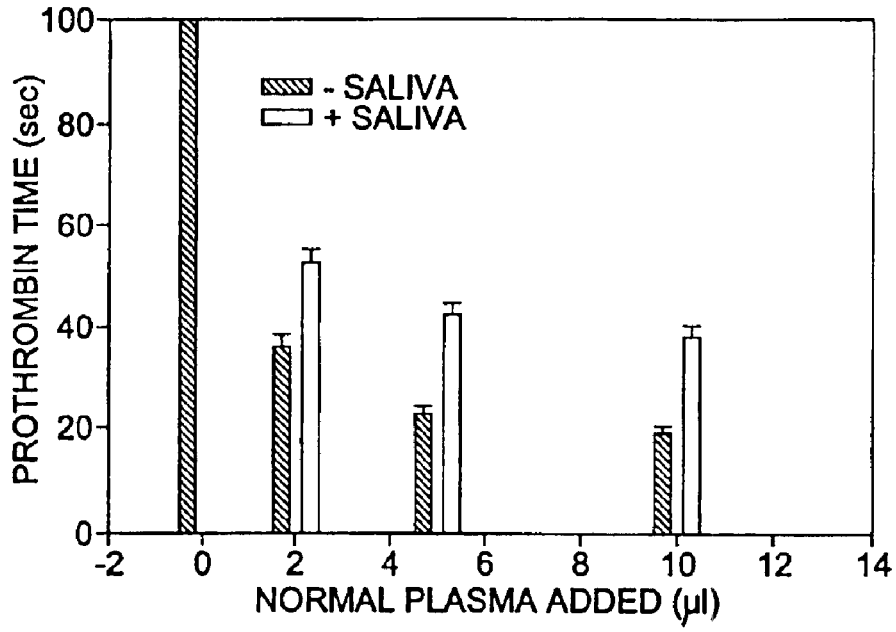
FIG. 3 shows the effect of *H. irritans* saliva on clotting of Factor II deficient plasma.

Inhibition of clotting in the TT assay by horn fly saliva indicates that a reaction occurring after the formation of thrombin is targeted. Two reactions occur after that point —1) the formation of fibrin monomers by the action of thrombin (factor II) on fibrinogen and 2) the cross-linking of fibrin monomers by the action of factor XIII. Thrombin is also involved in the activation of factor XIII. Thus, thrombin (factor II) was a probable target of horn fly saliva. To test this possibility, clotting times of plasma that had been depleted of factor II by using specific antibodies (Sigma-Aldrich® Co., St. Louis, Mo.) were determined. Addition of increasing amounts of normal plasma, (containing factor II), decreased the time for clotting as measured by the PTT assay (FIG. 3, −saliva). When horn fly saliva (equivalent to 2 flies) was added with the increasing amounts of normal plasma (FIG. 3, +saliva), the percentage delay in clotting time increased with increasing amounts of factor II (present in normal plasma). This pattern indicated that saliva contained a specific inhibitor of factor II.

Figure 4:
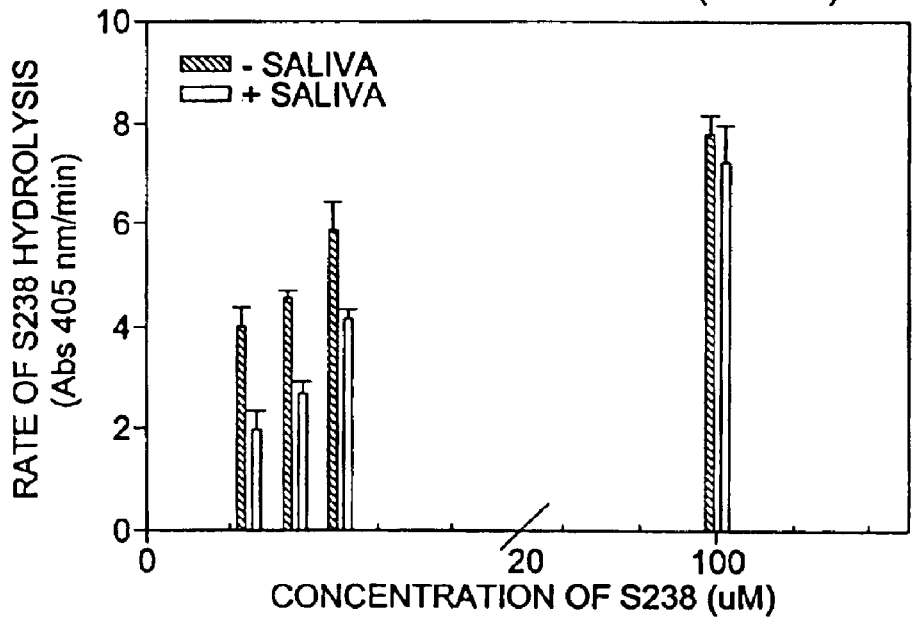
FIG. 4 shows inhibition of thrombin hydrolysis of S238 by *H. irritans* saliva.

Thrombin clotting action can be measured using a synthetic substrate (S238, American Diagnostica® Inc., Greenwich, Conn.) that produces a chromophore following hydrolysis by thrombin. The rates of hydrolysis of S238 by bovine thrombin alone (250 pM; FIG. 4, −saliva) and in the presence of horn fly saliva (equivalent to 2 flies) were measured at increasing concentrations of substrate over the range of 2.5–100 $\mu$M. These data confirmed the observation that horn fly saliva contains an inhibitor of thrombin and indicate that it may be a competitive inhibitor, as its effect is diminished when substrate is unlimited (100 $\mu$M). Several models can account for such biochemical behavior (Segel (1976) Biochemical Calculations, John Wiley & Sons, New York). For analysis, a Dixon plot is generated by determining the velocity (v) of substrate hydrolysis by thrombin in the presence of different fixed concentrations of substrate, and plotting 1/v versus inhibitor concentration. This provides the means to identify the type of inhibition and to determine the inhibition constant, Ki.

Characterization of the Physical Properties of the Anti-Clotting Component(s) in Horn Fly Salivary Glands to Devise a Purification Plan APTT clotting times in Table 2 indicate that activity in SGE is diminished after sitting at room temperature for 60 minutes or when subjected to 100° C. for 5 minutes. The activity precipitates with ethanol, and is reasonably stable to treatment with acetonitrile/TFA and lyophilization. These physical attributes are consistent with a proteinaceous inhibitor that can be purified under standard HPLC procedures using acetonitrile/TFA gradient elution.

TABLE 2

Characterization of the physical properties of anti-clotting activity in *Haematobia irritans* salivary gland extracts.

| Treatment | APTT Clotting Time (Seconds) |
|---|---|
| Control | 52.3 |
| SGE-Time O | 62.6 |
| SGE-room temperature × 60 min | 56.8 |
| SGE-100° C. × 5 min | 55.2 |
| SGE-ethanol precipitate | 59.8 |
| SGE-ethanol supernatant | 50.1 |
| SGE-lyopholized | 57.0 |
| SGE-50% acetonitrile/0.1% TFA | 57.8 |

HPLC Purification and Recalcification Assay of HPLC Saliva Fractions

For analytical method development, saliva from 100 to 150 flies was pooled for each HPLC run. For preparative separation, saliva from more than 500 flies was used for each run. Before injection onto the column, pooled saliva was always diluted with the initial solvent of the paired gradient Åsolvents. A macrosphere, C18, 4.6×250 mm, 300 Å column (AllTech) was used for all H PLC preparations. Protein elution was monitored by UV absorption at 220 nM, which detects peptide bonds. Components eluted from the column were collected at 0.5 or 1 minute intervals. An aliquot for activity assays was transferred from each fraction to a second tube containing bovine serum albumin (BSA) before lyophilization of all samples to remove organic solvents. Fractions dried with BSA (used to increase solubilization of purified protein) were reconstituted with Tris buffer (5 mM tris, 150 mM NaCl, pH 7.4 at 37° C.). Inhibitory activity in fractions was defined by the delay in clot formation using the above-described recalcification assay.

FIGS. 5A, 5B, and 5C depict the three reversed phase HPLC column procedures used to obtain a highly pure preparation of anti-clotting activity. Black lines are HPLC chromatograms, while the gray bars indicate clotting times of recalcification assay. FIG. 5A shows HPLC separation of *H. irritans* saliva using gradient elution (acetonitrile, 2-propanol, and TFA). FIG. 5B shows HPLC separation of fraction with maximum anticlotting activity in "A" using gradient elution (acetonitrile and TFA). FIG. 5C shows HPLC separation of fraction with maximum anticlotting activity in "B" using gradient elution (acetonitrile and HCl). Clotting data from the first fractionation run (A) indicated that horn fly saliva contains only one clotting inhibitor that elutes at approximately 45 minutes under the conditions used. For secondary HPLC separation, fractions from the target peak were combined and injected directly onto the column after the column had been equilibrated with the initial solvent. Anti-coagulant activity was retained after 3 consecutive HPLC runs, vacuum drying, and storage for 4 days at 4° C.

Figure 6:
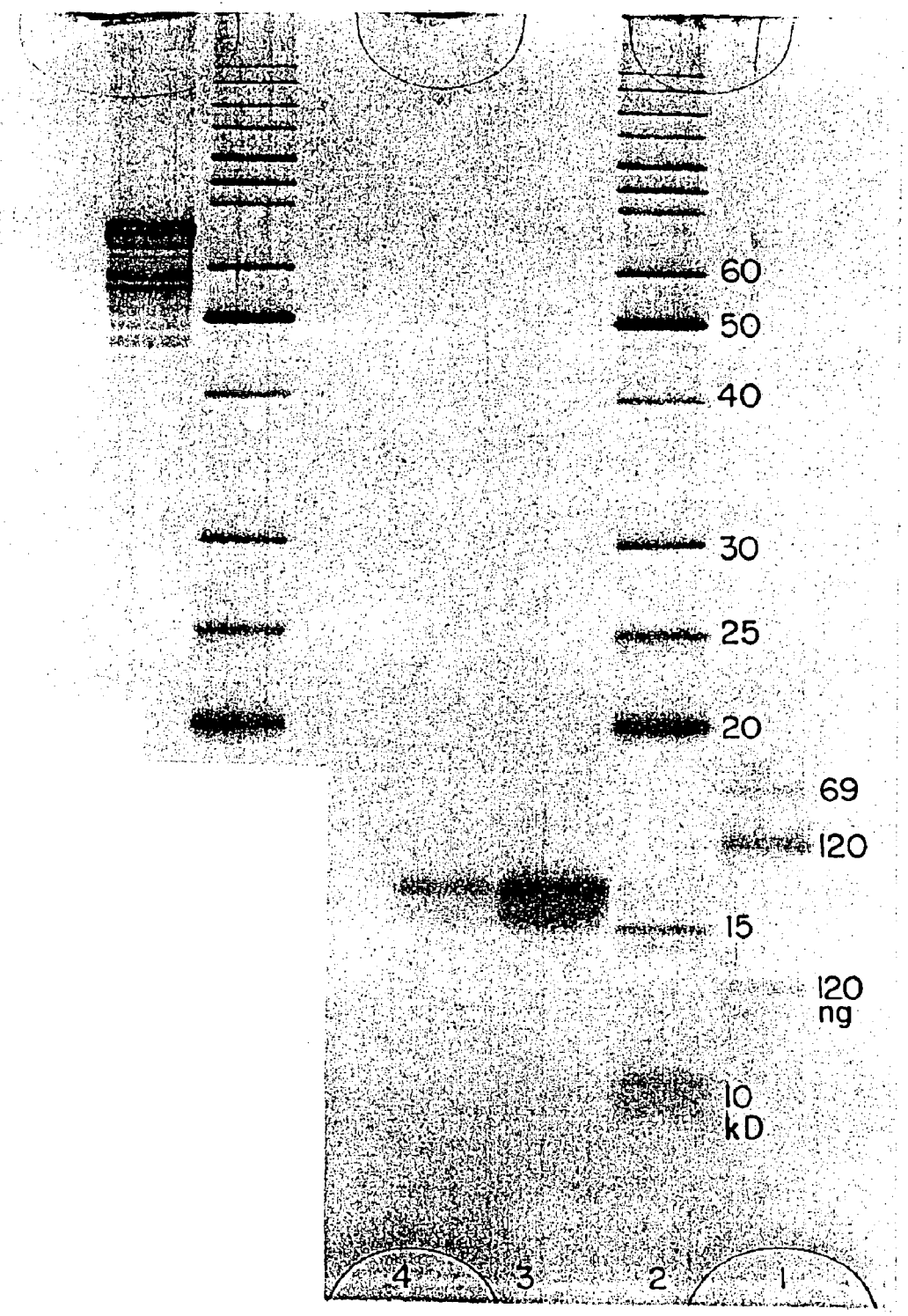
FIG. 6 shows SDS PAGE profile of HPLC purified salivary anticlotting protein thrombostasin.

FIG. 6 shows SDS-PAGE of horn fly salivary anticlotting protein after the 3-step HPLC separation. Lane 1 contained protein concentration marker; lane 2, protein molecular weight standard marker; lane 3, the HPLC fraction with higher anticlotting activity (FIG. 5-C) and lane 4, the HPLC fraction with lower anticlotting activity (FIG. 5-C). This profile indicated a single protein of high purity with a relative mobility of ≈16.5 KDa.

Construction of a Horn Fly Salivary Gland cDNA Library

Total salivary gland RNA (stored in several aliquots at −70° C. for a period of ≈3 years) was thawed, pooled and mRNA isolated using poly(A) Quick® reagents (Stratagene® Corporation, LaJolla, Calif.). A cDNA library was constructed using a ZAP express™ vector and kit from Stratagene® Corporation. Preliminary analysis of numbers of inserts indicated that a relatively small number of primary inserts was obtained (≈3×10$^4$). Approximately ⅕ of the primary library was reserved and the remainder used for one round of amplification to yield a titer of 5.1×10$^6$ plaque forming units (PFU) per ml.

Cloning the cDNA Coding for Thrombostasin

An estimated 110 pmoles of HPLC-pure thrombostasin were sent to Harvard Microchemistry Lab to obtain a precise molecular mass by mass spectroscopy and identification of 30 residues of the amino-terminal (N-) sequence. Although our analysis by SDS/PAGE consistently indicated a mass of ≈16.5 KDa (see, for example, FIG. 6), mass spectroscopy of the HPLC-pure sample detected an apparent "family" of 4 proteins with an average mass of 9.3±0.06 KDa. One N-terminal sequence was obtained from the ~9 KDa protein (SEQ ID NO: 3), indicating that the variable masses were obtained from largely identical proteins that may have variable ion pairs or that differ by as few as 1–2 amino acids. The sequence from the N-terminus also suggested that the protein is highly acidic. A second sample of thrombostasin, which was purified by HPLC and sent for analysis, yielded a similar mass. The unused remainder of this second sample was re-analyzed by SDS/PAGE. Again, the protein ran as a ~16.5 mass. Search of the scientific literature revealed another report of highly acidic protein that produced an anomalously high molecular mass when analyzed by PAGE (Takano et al. (1988) *Biochemistry* 27:1964–1972). In order to confirm the molecular mass, a third batch of thrombostasin with confirmed activity in a re-calcification assay, was subjected to SDS/PAGE. The single band of ~16.5 KDa protein was transferred to a PVDF membrane. The blot was stained with ponceau S to reveal the transferred thrombostasin band. This band and a control region of similar area was excised and sent to the Harvard Lab for sequence analysis. The N-terminal sequence from this analysis (SAGPI) confirmed the identity of the first 5 amino acids of the N-terminus.

The N-terminal sequence obtained from the first 30 residues of thrombostasin as set forth in SEQ ID NO: 3 was used to construct degenerate nucleotide primers by the Scott-Ritchey Research Center (SRRC) DNA lab at Auburn University. For template DNA, an aliquot of the *Haematobia irritans* salivary gland cDNA was used that had been removed and frozen at −20° C. following first strand cDNA synthesis for the above-described library construction. A PCR reaction using this template, the degenerate forward primer designed from thrombostasin N-terminal sequence and a reverse primer of oligo dT, yielded a product of approximately 350 base pairs. A 1 µl aliquot of the PCR product was used in a ligation reaction with the PCR 2.1 vector (Invitrogen® Corporation, San Diego, Calif.) at 14° C. overnight. OneShot™ competent cells (Invitrogen® Corporation) were then transformed with the ligation product and transferred onto LB agar plates containing ampicillin. Following overnight growth, blue and white colonies were visible representing cells containing plasmid without an insert (blue) and plasmids with an insert that disrupted the beta-galactosidase gene (white colonies). Ten white and 2 blue colonies were picked for amplification in liquid culture by overnight growth at ~30° C. Aliquots of each culture were preserved by storage in glycerol at −70° C. Plasmid size was estimated visually by ethidium bromide staining and comparison to molecular weight markers. DNA minipreps were prepared and sequenced by the SRRC DNA lab using primers based on sequences in the plasmid vector flanking the multiple cloning insertion site.

Analysis of the deduced amino acid sequence of the protein, set forth in SEQ ID NO: 2, coded for by the PCR-cloned cDNA set forth in SEQ ID NO: 1, confirmed identity to thrombostasin; i.e. the cDNA codes for a ~9 KDa protein and includes all the amino acids revealed by N-terminal sequencing, even though only a portion of that information was used in the synthesis of degenerate primers that permitted amplification by PCR. Twenty-one percent of the putative protein is comprised of aspartic and glutamic acid residues. This information also confirmed that the cDNA encoding active thrombostasin is contained in the *H. irritans* cDNA library. A search of protein databases in GenBank revealed no similar sequences.

Preparation of a Digoxigenin-Labeled Thrombostasin Probe

The above-described PCR-cloned thrombostasin cDNA fragment was used to produce a digoxigenin-labeled probe for screening the *H. irritans* cDNA library under very stringent conditions. A digoxigenin-labeled primer was synthesized by PCR using the cloned thrombostasin fragment as template and the Genius™ system (Boehringer Mannheim® Corporation, Indianapolis, Ind.) in a 1:5 digoxigenin-11-dUTP to dTTP ratio. The digoxigenin-labeled DNA was purified by agarose gel electrophoresis. Yield of labeled probe was estimated by titration and visual comparison to a DIG-labeled control DNA provided in the Genius™ Kit.

Cloning and Sequencing of a Full-Length cDNA

XL1 blue cells were transfected with 50,000 plaque forming units (pfu) from the amplified library and plated on a 150-mm NZY plate. Following overnight incubation, the plate was chilled for 2 hr at +4° C. before plaque lifts made in duplicate with nylon membranes and probed with the digoxigenin-labeled DNA fragment. In brief, "lifted" DNA was denatured for 5 min at RT, dried for 5 min, neutralized 5 min and cross linked in a Stratalinker® 1800 (Stratagene® Corp., La Jolla, Calif.) on autolink cycle; pre-hybridization and hybridization was in 5×SSC, 0.1% N-lauroylsarcosine, 0.02% SDS, 2% blocking reagent and 50% formamide at 65 EC; membranes were washed 4 times before visualization of the hybridized DIG-thrombostasin by incubation with anti-digoxigenin conjugated to alkaline phosphatase followed by substrate which produces a blue colored product. Several plaque picks from the first screening were subcloned to confirm positive clones in a secondary screen. Phage was extracted from the plaque picks in SM buffer and amplified by growth in XL1-Blue MRF cells on NZY plates as described above. DNA was isolated in minipreps of bacterial colonies grown overnight. Positive clones were tested by PCR amplification with thrombostasin-specific forward and reverse internal primers which were synthesized based on sequence in the cloned PCR fragment. Positive clones were further tested by an additional plaque assay and shown to be pure by hybridization of all colonies with the DIG/labeled probe.

Phagemids containing cloned inserts were obtained by automatic excision using the ExAssist®/XLOLR system and protocol of Stratagene® Corp. Colonies were grown on LB-kanamycin plates and glycerol stocks prepared for storage at −70° C. Similar colonies were picked for amplification by overnight growth. DNA was extracted in minipreps and analyzed by automated cycle sequencing (SRRC) in the forward direction using primers T3 and thrombostasin-F1 and in the reverse directions using primers T7 and thrombostasin-R1, and with forward and reverse primers to sequences internal to the termini. Several cDNA clones were obtained and sequenced. The nucleotide sequences for a partial cDNA designated TB8 are set forth in SEQ ID NO: 4, and the amino acid sequence encoded therein are set forth in SEQ ID NO:5. It is noted that amino acid residues 88–168 set forth in SEQ ID NO:5 encoded by nucleotides 263–505 set forth in SEQ ID NO:4 correspond to active thrombostasin.

The Wisconsin Package™ of the Genetics Computer Group (GCG, Madison Wis.) was used to analyze nucleic acid and putative protein sequences of thrombostasin cDNA.

To obtain the full length cDNA sequence, a 5' RACE (Rapid Amplification of cDNA Ends) procedure was employed, utilizing salivary gland mRNA and internal primers having 3' consensus sequence corresponding to the cDNA clones described above. Overlapping sequences were compiled to determine a composite full length cDNA sequence. The cDNA clone TB8 described above was used to construct a full length cDNA encoding thrombostasin, by adapting the clone to contain the 5' end nucleotides determined from the 5' RACE procedure. The nucleotide sequences for the full length cDNA are set forth in SEQ ID NO:6 and the amino acid sequences encoded therein is set forth are SEQ ID NO:7. It is noted that amino acid residues 95–175 set forth in SEQ ID NO: 7 encoded by nucleotides 283–525 set forth in SEQ ID NO:6 correspond to active thrombostasin.

Production of a Recombinant Thrombostasin (r-thrombostasin) Protein

Thrombostasin plasmid DNA and the transfer vector pBacPAK8 (CLONTECH®, Palo Alto, Calif.) were digested with 2 restriction enzymes that cut in the plasmid's multi-cloning sites but not internal sequences of thrombostasin. Excised thrombostasin and linearlized pBacPAK8 were purified by TAE gel electrophoresis. Digested bands were excised and DNA extracted with Sephaglas® Band Prep Kit (Pharmacia Biotech™, Uppsala, Sweden). A 1:2 (vector:insert) ligation reaction was setup to run overnight at 15° C. OneShot™ cells were transformed with the BacPAK8 plasmid containing the thrombostasin insert as described for the PCR fragment. Transformed cells were grown overnight on LB ampicillin plates. Several colonies were selected for liquid, overnight growth at 37° C. Glycerol stocks were prepared and frozen at −70° C. and plasmid quick preps made for size evaluation by agarose gel visualization. Miniprep DNA was prepared by column purification (Qiagen® Corp., Santa Clarita, Calif.) for DNA sequencing using the Bac 2 primer (CLONTECH® Laboratories. Inc.).

A recombinant baculovirus containing the thrombostasin insert was generated by co-transfection of Sf9 cells with BacPAK8/thrombostasin plasmid TB8/3 and Bsu36I digested BacPAK6 viral DNA using Lipofectin™ transfection reagent (Life Technologies™, Grand Island, N.Y.) and High Five™ Serum-Free Medium (Invitrogen® Corp., Carlsbad, Calif.). Controls included wild type virus (positive control) and plasmid DNA only (negative control). Cells were incubated with transfection medium for 5 hr at room temperature before adding TNM-FH medium containing 10% fetal bovine serum (TNM-FH/FBS), and further incubated at 27° C. for 72 hrs. Cell culture supernatant containing virus was collected and stored at 4° C. A plaque assay was performed to isolate pure thrombostasin-virus clones from the cell supernatant. Thirty-five nun plates containing $1.5 \times 10^6$ Sf9 cells each were infected in duplicate with 100 $\mu$l of supematant or a dilution up to $10^{-3}$ in a 100 $\mu$l volume of TNM-FH/FBS medium. After sitting for 1 hr at room temperature, infection medium was removed and the cells overlaid with 3.5 ml each of Grace's medium (Life Technologies™, Grand Island, N.Y.), containing 10% FBS, 50 $\mu$g/ml Gentamicin and 1% agarose. Cells were incubated in a plastic storage box with moist paper towels at 27° C. After 5 days, a second overlay was added that also included 0.16 mg/ml neutral red dye and 250 $\mu$g/ml Xgal. After the agarose overlay formed a gel, the dishes were inverted and incubated for 48 hr at room temperature. Clear, positive plaques were picked and virus eluted by incubation overnight in TNM-FH medium. Sf9 cells were infected with eluted virus and incubated for 4 days at 27° C. to generate passage 1 virus.

Cells were collected in phosphate buffered saline (10 mM, pH 7.4) and DNA extracted using the Stratagene® Corporation DNA micro extraction kit and protocol II in the instruction manual. Extracted DNA was used as template for PCR with a thrombostasin forward and reverse primer pair and the Bac1/Bac2 primer pair (CLONTECH® Laboratories, Inc.). Amplification with both primer pairs assured that the correct transformation event occurred. A secondary plaque assay was conducted to assure clone purity, and to determine virus titer.

Characterization of r-thrombostasin Production

Sf9 cells were infected with virus (multiplicity of infection=2) and incubated at 27° C. until media are collected at 12, 24, 48, 72 and 96 hr. Virus is concentrated and removed from media by centrifugation in Centriplus™ 100 concentrators (Amicon® Corporation, Beverly, Mass.) at 3,000×g for 2 hr at room temperature. Total protein in the <100 KDa fraction is estimated by the modified Lowry Assay (Sigma-Aldrich® Co., St. Louis, Mo.).

Anti-clotting and/or antithrombin activity of r-thrombostasin is tested using the chromogenic substrate S238 assay as described above.

Purification of r-thrombostasin by RP/HPLC

Large molecular weight components ($\geq 10$ KDa) in the virus-free cell culture supernatant are concentrated by centrifugation at 3,000×g for 4 hr in Centriplus™ 10 microconcentrators. RP/HPLC using a C18 macrosphere column and elution with an acetonitrile gradient is used for isolation of r-thrombostasin from other medium components as described above.

Immunogenic properties of thrombostasin in a laboratory animal model (rabbits) as the first step toward production of a nucleic acid (DNA) vaccine against horn fly blood-feeding.

Anti-hemostatic proteins in the saliva of blood-feeding insects are not highly immunogenic (see Cupp and Cupp (1997) *J. Med. Entomol.* 34:87–94). This experimental observation agrees with the intuitive concept that generation of an immune response, especially production of neutralizing antibody, might prevent or decrease blood feeding and production of progeny and fitness. Thus, it is important to develop methods to elicit a robust immune response to such molecules. Moreover, effective immunization of cattle in the field also requires a practical vaccine that needs a minimum of handling and storage. In the past few years, immunization with nucleic acids has been demonstrated to generate strong immune responses to encoded proteins that can be directed to specific immune compartments by the location and/or amount of nucleic acid administered. Such vaccines, composed of plasmids with the DNA of interest inserted, can be produced at low cost and by relative simple techniques of bacterial culture; they are stable to storage at room temperature and thus circumvent many of the problems of protein-based vaccines. Thus, initially, immunization of rabbits is tested with thrombostasin nucleic acid.

A vaccine plasmid is constructed containing the CMV promoter and kanamycin resistance for selection. The procedures for restriction digestion and re-ligation of the baculovirus transfer vector as described above is used to produce the thrombostasin containing vaccine plasmid (TS-Vac).

Serum, serving as pre-immunization control, is obtained from blood samples taken from each rabbit via the large ear vein. Nine rabbits are injected intradermally with one of three TS-Vac plasmids in PBS (500 μg of plasmid with no insert=control; 200 μg, or 500 μg TS-Vac=test plasmids). Blood is sampled after approximately 4 weeks and tested for humoral (the presence of specific antibody titer) and cellular response (blastogenic response) to thrombostasin. These parameters are monitored on a weekly basis thereafter up to 20 weeks post-injection. All immunological assays used are standard and have been used in previously published work on immune response to salivary factors of blood-feeding insects (Cross et al. (1993) *J. Med. Entomol.* 30:725–734; Cross et al. (1993) *J. Med. Entomol.* 30:928–935).

Antibody titer is determined by a direct ELISA assay (Cross et al. (1993) *J. Med. Entomol.* 30:725–734; Cross et al. (1993) *J. Med. Entomol.* 30:928–93 5). Briefly, 96 well flat-bottomed microtiter plates are coated with r-thrombostasin, or non-specific protein, then blocked with 1% bovine serum albumin (BSA) in PBS. Wells are incubated with pre-immune sera or test sera, then washed with PBS-tween before addition of alkaline phosphatase-conjugated anti-rabbit IgG (Sigma-Aldrich® Co., St. Louis, Mo.) or anti-rabbit IgM (Southern Biotechnology Assoc. Inc., Birmingham, Ala.) Following substrate reaction with p-nitrophenyl phosphate (pNPP), color intensity is read at 405 nm using a Spectramax® microtiter plate reader (Molecular Devices® Corporation, Sunnyvale, Calif.). Antibody titer is calculated and compared among treatments to determine the optimum amount of immunogen for antibody generation.

Antibody is evaluated for specificity to thrombostasin by dot blot (Cross et at. (1993) *J. Med. Entomol.* 30:725–734) using r-thrombostasin. R-thrombostasin, or bovine serum albumin (BSA) control is dotted onto wells of 96-well nitrocellulose-bottomed microtiter plates (Millipore® Corporation, Marlborough, Mass.). Non-fat milk (3%) in PBS is used as a blocking solution. Test sera are added and incubated for 1 hr before washing and substrate reaction. Specificity of reaction is determined by visual inspection.

Cellular response to thrombostasin is tested using peripheral blood mononuclear cells (PBM) isolated by Ficoll-Paque centrifugation of blood collected in EDTA as anticoagulant (Ramachandra & Wikel (1992) *J. Med. Entomol.* 29:818–826). Viability of isolated cells is determined on an aliquot using fluorescein diacetate (FDA; Sigma-Aldrich® Co., St. Louis, Mo.) which brightly labels healthy cells. PBM are added at $5\times10^5$ cells/well of a microtiter plate before addition of r-thrombostasin, horn fly saliva or non-specific protein. The mitogen ConA is added and incubation continued for 72 hr. Cellular response to test protein is determined using the MTT colorimetric assay (Denizot and Land (1986) *J. Immunol. Methods.* 89(2):271–277) which is read in the Spectramax® microtiter plate reader (Molecular Devices® Corporation. Sunnyvale, Calif.) at 570 nm. Blastogenic response to thrombostasin is determined by increase over control. Comparison of response in the presence of whole saliva can monitor for immunomodulating factors in saliva.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Other modifications and embodiments of the invention will come to mind in one skilled in the art to which this invention pertains having the benefit of the teachings presented herein. Therefore, it is to be understood that the invention is not to be limited to the specific embodiments disclosed. Although specific terms are employed, they are used in generic and descriptive sense only and not for purposes of limitation, and that modifications and embodiments are intended to be included within the scope of the appended claims.

That which is claimed:

1. A purified protein having antithrombin activity, wherein said protein comprises an amino acid sequence that is at least 80% identical to the amino acid sequence set forth in SEQ ID NO:2, SEQ ID NO:5, or SEQ ID NO:7.

2. The protein of claim 1, wherein said protein comprises an amino acid sequence that is at least 90% identical to the amino acid sequence set forth in SEQ ID NO:2, SEQ ID NO:5, or SEQ ID NO:7.

3. The protein of claim 2, wherein said protein comprises the amino acid sequence set forth in SEQ ID NO:2, SEQ ID NO:5, or SEQ ID NO:7.

4. The protein of claim 1, wherein said protein is produced by recombinant methods.

5. The protein of claim 1, wherein said protein modulates the immune response.

6. A pharmacological composition comprising a therapeutically effective amount of the protein of claim 1.

7. A purified protein having antithrombin activity, wherein said protein comprises an amino acid sequence that is at least 95% identical to the amino acid sequence set forth in SEQ ID NO: 2, SEQ ID NO: 5, or SEQ ID NO: 7.

8. The protein of claim 7, wherein said protein is produced by recombinant methods.

9. The protein of claim 7, wherein said protein modulates the immune response.

10. A pharmacological composition comprising a therapeutically effective amount of the protein of claim 7.

11. A purified protein that has antithrombin activity, wherein said protein comprises an amino acid sequence that comprises at least 15 contiguous amino acids of the sequence set forth in SEQ ID NO:2, SEQ ID NO: 5, or SEQ ID NO: 7.

12. The protein of claim 11, wherein said protein comprises an amino acid sequence that comprises at least 15 contiguous amino acids of the sequence set forth in SEQ ID NO:7 between amino acid residue 95 and amino acid residue 175.

13. The protein of claim 11, wherein said protein comprises an amino acid sequence that comprises at least 30 contiguous amino acids of the sequence set forth in SEQ ID NO:2, SEQ ID NO: 5, or SEQ ID NO: 7.

* * * * *

UNITED STATES PATENT AND TRADEMARK OFFICE
CERTIFICATE OF CORRECTION

PATENT NO. : 6,927,279 B2
DATED : August 9, 2005
INVENTOR(S) : Cupp et al.

It is certified that error appears in the above-identified patent and that said Letters Patent is hereby corrected as shown below:

<u>Column 1,</u>
Line 12, before "FIELD OF INVENTION" insert:
-- FEDERALLY SPONSORED RESEARCH OR DEVELOPMENT
　　This invention was made with government support under Grant No. USDA-96-35302-3381 awarded by the United States Department of Agriculture. The government has certain rights in the invention. --.

Signed and Sealed this

Third Day of January, 2006

JON W. DUDAS
*Director of the United States Patent and Trademark Office*